US006020288A

United States Patent [19]
Nonomura et al.

[11] Patent Number: 6,020,288
[45] Date of Patent: Feb. 1, 2000

[54] METHODS AND COMPOSITIONS FOR ENHANCING CYTOCHROME P450 IN PLANTS

[76] Inventors: Arthur M. Nonomura, 311 Depot Rd., Boxborough, Mass. 01719; Andrew A. Benson, 6044 Folsom Dr., La Jolla, Calif. 92037; John N. Nishio, 519 S. 8th St., Laramie, Wyo. 82070-3917

[21] Appl. No.: 08/927,415

[22] Filed: Sep. 11, 1997

Related U.S. Application Data

[63] Continuation-in-part of application No. 08/610,928, Mar. 5, 1996, Pat. No. 5,846,908, which is a continuation-in-part of application No. 08/399,399, Mar. 6, 1995, abandoned, which is a continuation-in-part of application No. 08/351,348, Dec. 9, 1994, Pat. No. 5,597,400, which is a continuation-in-part of application No. 07/901,366, Jun. 19, 1992, abandoned.

[51] Int. Cl.$^7$ ............................ A01N 31/00; A01N 37/00; A01N 43/22; A01N 57/02
[52] U.S. Cl. .......................... 504/127; 504/128; 504/130; 504/136; 504/138; 504/140; 504/142; 504/143; 504/144; 504/149
[58] Field of Search ..................... 504/127, 128, 504/130, 136, 138, 140, 142, 143, 144, 149

[56] References Cited

U.S. PATENT DOCUMENTS

| | | | |
|---|---|---|---|
| 3,897,241 | 7/1975 | Washio et al. | 71/113 |
| 4,799,953 | 1/1989 | Danzig et al. | 71/98 |
| 4,846,877 | 7/1989 | Azuma et al. | 71/92 |
| 5,298,482 | 3/1994 | Tanaka et al. | 504/320 |
| 5,300,540 | 4/1994 | Masters | 523/309 |
| 5,532,204 | 7/1996 | Joshi | 504/118 |
| 5,597,400 | 1/1997 | Nonomura et al. | 71/28 |

FOREIGN PATENT DOCUMENTS

| | | |
|---|---|---|
| 0 465 907 A1 | 1/1992 | European Pat. Off. . |
| 2689905 | 10/1993 | France . |
| 2004856 | 4/1979 | United Kingdom . |

OTHER PUBLICATIONS

Whitlock, J.P. et al. Induction of Cytochrome P450 Enzymes That Metabolize Xenobiotics. Chapter 10 in Cytochrome P450: Structure, Mechanism and Biochemistry, 2nd ed. Ortiz de Montellano, ed. 1995, pp. 367–389.

Porter, T.D. et al. Chytochrome P–450. The Journal of Biological Chemistry. Jul. 25, 1991, vol. 266, No. 21 pp. 13469–13472.

Bollwell, G.P. et al. Plant Cytochrome P450. Phytochemistry. 1994, vol. 37, No. 6, pp. 1491–1506.

Schuler, M.A. Plant Cytochrome P450 Monooxygenases. Critical Reviews in Plant Sciences. 1996, vol. 15, No. 3, pp. 235–284.

Halkier, B.A. et al. Involvement o Cytochrome P–450 in the Biosynthesis of Dhurrin in Sorghum bicolor (L.) Moench. Plant Physiology. 1991, vol. 96, pp. 10–17.

Aharoni, A. et al., "Isolation and Characterization of Cytochrome P–450 cDNAs from Strawberry Fruit" *17th Intl. Congress of Biochem. and Molec. Biol.*, San Francisco, CA, p. A811, Abstract No. P233 (Aug. 24–29, 1997).

Angerhorfer, A. and Bittl, R., "Radicals and Radical Pairs in Photosynthesis" *Photochem. Photobiol.* 63(1):11–38 (1996).

Badger, M.R. and Schrieber, U., "Effects of inorganic carbon accumulation on photosynthetic oxygen reduction and cyclic electron flow in the cyanobacterium Synechococcus PCC7942" *Photosynthesis Res.* 37:177–191 (1993).

Bolwell, G.P. et al., "Plant Cytochrome P450" *Phytochemistry* 37(6):1491–1506 (1994).

(List continued on next page.)

*Primary Examiner*—S. Mark Clardy
*Attorney, Agent, or Firm*—Nields, Lemack & Dingman

[57] ABSTRACT

The present invention provides methods for treating plants which comprise application of an oxidant that induces NADPH:cytochrome P450 reductase and application of a reductant that induces cytochrome P450 monooxygenase. The present invention also provides methods for increasing cytochrome P450 in plants and for enhancing the growth of plants. The present invention also provides compositions and systems useful in the methods of the present invention.

38 Claims, 1 Drawing Sheet

OTHER PUBLICATIONS

Bowling, S.A. et al., "A mutation in Arabidopsis that leads to constitutive Expression of systemic acquired resistance" *The Plant Cell* 6:1845–1857 (Dec. 1994).

Butler, J. and Hoey, B.M., "The one–electron reduction potential of several substrates can be related to their reduction rates by cytochrome P–450 reductase" *Biochimica et Biophysica Acta* 1161:73–78 (1993).

Nee, M.W. and Bruice, T.C., "Use of the N–Oxide of p–Cyano–N,N–dimethylaniline as an "Oxygen" Donor in a Cytochrome P–450 Model System" *J. Am. Chem. Soc.* 104(22):6123–6125 (1982).

Nonomura, A.M. and Benson, A.A., "The path of carbon in photosynthesis: Improved crop yields with methanol" *Proc. Natl. Acad. Sci. USA* 89:9794–9798 (1992).

Ohkawa, H. et al., "Genetically Engineered Plants Expressing Mammalian P450 Monooxygenases for Phytoremediation" *17th Intl. Congress of Biochem. and Molec. Biol.*, San Francisco, CA, Abstract No. P37 (Aug. 24–29, 1997).

Palazon, J. et al., "Effects of Auxin and Phenobarbital on Morphogenesis and Production of Digitoxin in Digitalis callus" *Plant Cell Physiol.* 36(2):247–252 (1995).

Parikh, A. et al., "Drug metabolism by *Escherichia coli* expressing human cytochromes P450" *Nature Biotechnol.* 15:784–788 (1997).

Porter, T.D. and Coon, M.J., "Cytochrome P–450" *J. Biol. Chem.* 266:13469–13472 (1991).

Sasame, H.A. and Gillette, J.R., "Studies on the Relationship between the Effects of Various Substances on Absorption Spectrum of Cytochrome P–450 and the Reduction of p–Nitrobenzoate by Mouse Liver Microsomes" *Mol. Pharmacol.* 5:123–130 (1969).

Schuler, M.A., "Plant Cytochrome P450 Monooxygenases" *Crit. Rev. Plant Sci.* 15(3):235–284 (1996).

Sherry, B. and Abeles, R.H., "Mechanism of Action of Methanol Oxidase, Reconstitution of Methanol Oxidase with 5–Deazaflavin, and Inactivation of Methanol Oxidase by Cyclopropanol" *Biochem.* 24(11):2594–2605 (1985).

Strobel, H.W. et al., "NADPH Cytochrome P450 Reductase and Its Structural and Functional Domains" in: Cytochrome P450, Structure, Mechanism, and Biochemistry, Second Edition, Paul R. Ortiz de Montellano, Ed., Plenum Press, NY, pp. 225–390 (1995).

Szekeres, M. et al., "Brassinosteroids Rescue the Deficiency of CYP90, a Cytochrome P450, Controlling Cell Elongation and De–etiolation in Arabidopsis" *Cell* 85:171–182 (1996).

Takabe, T., "Glycolate Formation Catalyzed by Spinach Leaf Transketolase Utilizing the Superoxide Radical" *Biochem.* 19:3985–3989 (1980).

Tolbert, N.E. et al., "The oxygen and carbon dioxide compensation points of $C_3$ plants: Possible role in regulating atmospheric oxygen" *Proc. Natl. Acad. Sci. USA* 92:11230–11233 (1995).

Wachtveitl, J. et al., "Tyrosine 162 of the Photosynthetic Reaction Center L–Subunit Plays a Critical Role in the Cytochrome $C_2$ Mediated Rereduction of the Photooxidized Bacteriochlorophyll Dimer in *Rhodobacter sphaeroides*" *Biochem.* 32:10894–10904 (1993).

Wardman, P., "Reduction Potentials of One–Electron Couples Involving Free Radicals in Aqueous Solution" *J. Phys. Chem. Ref. Data* 18(4):1637–1755 (1989).

Wendler, C. et al., "Effect of Glufosinate (Phosphinothricin) and Inhibitors of Photorespiration on Photosynthesis and Ribulose–1,5–Bisphosphate Carboxylase Activity" *J. Plant Physiol.* 139:666–671 (1992).

Cottrell, S. et al., "Studies on the cytochrome P–450 of avocado (*Persa americana*) mesocarp microsomal fraction" *Xenobiotica* 20(7):711–726 (1990).

Damme, B. et al., "Induction of hepatic cytochrome P4502E1 in rats by acetylsalicylic acid or sodium salicylate" *Toxicology* 106:99–103 (1996).

Frey, M. et al., "Analysis of a Chemical Plant Defense Mechanism in Grasses" *Science* 277:696–699 (Aug. 1, 1997).

Gruber, V. et al., "Human haemoglobin from transgenic tobacco" *Nature* 386:29–30 (Mar. 6, 1997).

Halkier, B.A. and Moller, B.L., "Involvement of Cytochrome P–450 in the Biosynthesis of Dhurrin in *Sorghum bicolor* (L.) Moench" *Plant Physiol.* 96:10–17 (1991).

Hara, Y. et al., "Effect of Gibberellic Acid on Berberine and Tyrosine Accumulation in *Coptis japonica*" *Photochem.* 36(3):643–646 (1994).

He, S. et al., "The surface–exposed tyrosine residue Tyr83 of pea plastocyanin is involved in both binding and electron transfer reactions with cytochrome f" *EMBO J.* 10(13):4011–4016 (1991).

Holmberg, N. et al., "Transgenic tobacco expressing Vitreoscilla hemoglobin exhibits enhanced growth and altered metabolite production" *Nature Biotechnol.* 15:244–247 (Mar. 15, 1997).

Kärgel, E. et al., "*Candida maltosa* NADPH–cytochrome P450 Reductase: Cloning of a Full–length cDNA, Heterologous Expression in *Saccharomyces cerevisiae* and Function of the N–terminal Region for Membrane Anchoring and Proliferation of the Endoplasmic Reticulum" *Yeast* 12:333–348 (1996).

Klein, M.L. and Fulco, A.J., "Critical residues involved in FMN binding and catalytic activity in Cytochrome $P450_{BM-3}$" *J. Biol. Chem.* 268(10):7553–7561 (1993).

Koch, B.M. et al., "The Primary Sequence of Cytochrome P450tyr, the Multifunctional N–Hydroxylase Catalyzing the Conversion of L–Tyrosine to p–Hydroxyphenyacetaldehyde Oxime in the Biosynthesis of the Cyanogenic Glucoside Dhurrin in *Sorghum bicolor* (L.) Moench" *Archives Biochem. Biophys.* 323(1):177–186 (1995).

Kusukawa, M. and Iwamura, H., "N–(3,4–Methylenedioxyphenyl) carbamates as Potent Flower–Inducing Compounds in Asparagus Seedlings as well as Probes for Binding to Cytochrome P–450" *Z. Naturforsch* 50c:373–379 (1995).

Luo, M. et al., "Characterization of a Gene Family Encoding Abscisic Acid—and Environmental Stress–inducible Proteins of Alfalfa" *J. Biol. Chem.* 267(22):15367–15374 (1992).

MacDonald, G.M. et al., "A difference Fourier–transform infrared study of two redox–active tyrosine residues in photosystem II" *Proc. Natl. Acad. Sci. USA* 90:11024–11028 (Dec. 1993).

Miles, C.S. et al., "Tyr–143 facilitates interdomain electron transfer in flavocytochrome $b_2$" *Biochem. J.* 285:187–192 (1992).

Miller, A.G. and Canvin, D.T., "Glycolaldehyde Inhibits $CO_2$ Fixation in the Cyanobacterium Synechococcus UTEX 625 without Inhibiting the Accumulation of Inorganic Carbon or the Associated Quenching of Chlorophyll a Fluorescence" *Plant Physiol.* 91:1044–1049 (1989).

Moreland, D.E. et al., "Metabolism of Metolachlor by a Microsomal Fraction Isolated from Grain Sorghum (*Sorghum bicolor*) Shoots" *Z. Naturforsch* 45c:558–564 (1990).

METHODS AND COMPOSITIONS FOR ENHANCING CYTOCHROME P450 IN PLANTS

RELATED APPLICATIONS

This application is a continuation-in-part of U.S. patent application Ser. No. 08/610,928, filed Mar. 5, 1996, now U.S. Pat. No. 5,846,908, which is a continuation-in part of U.S. patent application Ser. No. 08/399,399, filed Mar. 6, 1995; which was a continuation-in part of Ser. No. 08/351,348 filed Dec. 9, 1994, now U.S. Pat. No. 5,597,400 issued on Jan. 28, 1997, which was a continuation-in-part of U.S. patent application Ser. No. 07/901,366, filed on Jun. 19, 1992. The full disclosures of each of these patent applications are incorporated herein by reference.

Related international application are PCT/US96/02444 (equivalent of Ser. No. 08/610,928) and PCT/US93/05676 (equivalent of Ser. No. 08/351,348).

BACKGROUND OF THE INVENTION

The present invention relates generally to methods and compositions for treating plants and for plant growth enhancement.

Photosynthesis is the process by which all photosynthetic plants utilize solar energy to build carbohydrates and other organic molecules from carbon dioxide ($CO_2$) and water. In general, photosynthesis is a complex sequence of electron and proton-transfer reactions leading to stable reduced metabolites; but when electrons or radicals accumulate along this chain, the resulting imbalance interferes with one after another system until growth decreases. The chemistry of living systems dictates that an electron acceptor is usually balanced by the presence of an electron donor, however, application of chemicals for biological response has generally been one-sided in the sense that xenobiotics are generally formulated without regard to balancing electron acceptors and donors. This historical one-sided approach often stresses the biological system when either oxidants or reductants abound. Our tests suggest that when a balance of electron couples is established by application of formulations selected for appropriate pairing, stress components may be neutralized. The $E_0$ values of the prospective couples are defined within a range that is compatible to biological systems. In sunlight, a nontoxic balance is especially important for minimizing damage by oxidants. Imbalances of electron couples may be corrected by induction of Cytochromes P450 (CYP) and NADPH:Cytochrome P450 reductase (CPR) pathways that result in the utilization of reducing power.

Cytochromes P450 are a superfamily of hemoproteins that catalyze the singular insertions of oxygen, i.e. monooxygenation, of endogenous and xenobiotic hydrophobic substrates, wherein, the general reaction for hydroxylation by the cytochromes P450 system is,

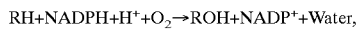

and R represents a substrate compound. The CYP and flavin monooxygenase families are noted for their broad substrate specificities and utilization of oxygen without being linked to phosphorylation of adenosine diphosphate (ADP) and can mediate hydroxylations at nitrogen and sulfur heteroatoms, epoxidations, dehalogenations, deaminations and dealkylations. In general, the monooxygenations require one or two additional proteins to transfer electrons from NADPH to the heme iron and these systems are placed in two groups: Class I, which use an iron-sulfur protein to shuttle electrons from FAD-containing reductase to CYP in mitochondria and bacteria; and Class II, in which NADPH:Cytochrome P450 reductase transfers electrons from NADPH to a CYP in microsomes. In plants, CYP comprises a wide range of hydroxylases, epoxidases, peroxidases and oxygenases which are largely based upon Class II monooxygenations.

Neither the direct connection of CYP and CPR to regulate photosynthesis nor the formulations of cytochromes P450 and inducer substrates have been made previously. We introduce novel methods for formulating compositions comprised of CYP and CPR substrates and enzymes selected for completing the necessary electron couples and inducing the enzymes. These formulations enhance plant growth, improve activity and prevent phytotoxicity.

For these reasons, it would be desirable to provide novel methods and formulations for activating cytochromes P450 enzymes. It would be particularly desirable if such methods and compositions were able to regulate plant growth (i.e., PGR). Additionally, it would be desirable if the compositions reduce toxicity of otherwise one-sided treatments. The present invention should further provide convenient methods resulting in increased activities of CYP and CPR electron couples for applying the novel compositions to plants. It is desirable that the methods and compositions of the present invention promote rapid growth and maturing of the treated plant, increase sugar content, improve blossoms and enhance the quality and quantity of plants. Furthermore, it is generally desirable to provide methods for enhancement of CYP and CPR related enzymes in all biological systems.

The structures and functions of CPR and CYP are reviewed with focus on animal CYP, some of which metabolize more than fifty structurally diverse compounds. See, e.g., H. W. Strobel, et al., "NADPH Cytochrome P450 Reductase and Its Structural and Functional Domains," and C. von Wachenfeldt, et al., "Structures of Eukaryotic Cytochrome P450 Enzymes," P. R. Ortiz de Montellano, ed. (1995) CYTOCHROME P450: STRUCTURE, MECHANISM, AND BIOCHEMISTRY (Second Edition), Plenum Press, New York. Inducers of cytochromes P450 in animal systems include aromatic hydrocarbons, proteins, phenobarbital, peroxisome proliferators, steroids, aminopyrine and ethanol (see, J. P. Whitlock et al., "Induction of Cytochrome P450 Enzymes That Metabolize Xenobiotics" in P. R. Ortiz de Montellano, ed. (1995) CYTOCHROME P450: STRUCTURE, MECHANISM, AND BIOCHEMISTRY (Second Edition), Plenum Press, New York, pp 367–390); but no inducers of cytochromes P450 for growth have been identified in green plant systems.

In avocado tissue, alcohols, aniline, p-chloro-N-methylaniline, N, N-dimethylaniline, cinnamic acid, dimethyl formamide, aryl hydrocarbons and fatty acids showed binding to cytochromes P450. See, S. Cottrell, et al., "Studies on the cytochrome P-450 of avocado (*Persa americana*) mesocarp microsomal fraction" Xenobiotica 20: 711–726 (1990). In recent reviews of molecular cloning, plant pathways included cytochromes P450 catalysis of oxygen insertion for fatty acids, phenylpropanoids, flavonoids, terpenoids, alkaloids, dyes, pesticides (see, e.g., G. P. Bolwell, et al., "Review Article Number 96. Plant Cytochrome P450" *Phytochemistry* 37: 1491–1506 (1994)); lignins, coumarins, pigments, alkaloids, jasmonates and plant growth regulators (see, M. A. Schuler "Plant Cytochrome P450 Monooxygenases" *Critical Reviews in Plant Sciences* 15(3): 235–284 (1996)). Metolachlor is a herbicide that is detoxified by cytochromes P450 (see, D. E. Moreland, et al., "Metabolism of Metolachlor by a Microsomal Fraction Isolated from Grain Sorghum (*Sorghum bicolor*) Shoots" *Z. Naturforsch* 45c: 558 (1990)). Beneficial effects of flower inducement implicate binding of carbamates to cytochromes P450 (see, M. Kusukawa, et al., "N-(3,4-Methylenedioxyphenyl)carbamates as Potent Flower-Inducing Compounds in Asparagus Seedlings as Well as Probes for Binding to Cytochrome P-450" *Z. Naturforsch* 50c: 373 (1995)), where known inhibitors of cytochromes P450 including piperonyl butoxide and trans-cinnamic acid 4-hydroxylase stopped the effect. The hormonal action of the ecdysone-like brassinosteroids that regulate various aspects of plant development is related to CYP90 genes (see, M. Szekeres, et al., "Brassinosteroids rescue the deficiency of CYP90, a cytochrome P450 controlling cell elongation and de-etiolation in Arabidopsis" *Cell (Cambridge)* 85: 171 (1996)). Salicylate and aspirin caused elevation of rat liver ethanol inducible cytochromes P450 (see, B. Damme, et al., "Induction of hepatic cytochrome P4502E1 in rats by acetylsalicylic acid or sodium salicylate" *Toxicology* 106: 99–103 (1996)) and, although salicylates in plants are associated with systemic acquired resistance, their relationships to plant cytochromes P450 has not been demonstrated (see, e.g., S. A. Bowling, et al., "A Mutation in Arabidopsis That Leads to Constitutive Expression of Systemic Acquired Resistance" *The Plant Cell* 6: 1845–1857 (1994)). Phenobarbital has been shown to enhance the activity of $CYP_{cc}$ in non-photosynthetic plant tissue cultures. See, J. Palazon, et al., "Effects of auxin and phenobarbital on morphogenesis and production of digitoxin in Digitalis callus" *Plant and Cell Physiology* 36: 247 (1995).

As a supplement to tissue culture, tyrosine has been found in specific natural products during fermentation. See, Y. Hara, et al., "Effect of gibberellic acid on berberine and tyrosine accumulation in Coptisjaponica" *Phytochemistry* 36: 643–646 (1994)). Tyrosine is essential for flavin mononucleotide binding to cytochromes P450, (see, M. L. Klein, et al., "Critical Residues Involved in FMN Binding and Catalytic Activity in Cytochrome $P450_{BM-3}$" *The Journal of Biochemistry* 268: 7553–7561 (1993)) and plays a key role in facilitating electron transfer between flavin mononucleotide and heme groups of other cytochromes (see, C. S. Miles, et al., "Tyr-143 facilitates interdomain electron transfer in flavocytochrome $b_2$" *Journal of Biochemistry* 285: 187–192 (1992)). Tyrosine is a substrate for CYP56 and CYP79 in plants. See, B. M. Koch, et al., "The primary sequence of cytochrome P450tyr, the multifunctional N-hydroxylase catalyzing the conversion of L-tyrosine of p-hydroxyphenylacetaldehyde oxime in the biosynthesis of the cyanogenic glucoside dhurrin in Sorghum bicolor (L.) Moench." *Archives of Biochemistry and Biophysics* 323: 177–186 (1995).

Among the early cytochromes P450 functional markers, para-nitrobenzoate (pNBA) was used to screen the activity of liver microsomal cytochromes P450 substrates by following the reduction to the primary amine. Thus, cytochrome P450 substrates were defined by type I spectra characterized by a trough at 420 nm and a peak at 385 nm or type II spectra characterized by a trough at 390 nm and a peak at 430 nm. See, H. A. Sasame, et al., "Studies on the Relationship between the Effects of Various Substances on Absorption Spectrum of Cytochrome P-450 and the Reduction of p-Nitrobenzoate by Mouse Liver Microsomes" *Mol. Pharmacol.* 5: 123 (1969); and J. R. Gillette "Reductive Enzymes" *Handbuch der experimentellen Pharmakologie* 28/2: 349 (1971). In addition to pNBA, other oxidants have been identified including menadione, Mitomycin C, Adriamycin, anthraquinone sulfonate, dinitrobenzene, and quinones, their association with cytochromes P450 dependent upon $E_0$ values residing within a range of −400 mV to −165 mV. See, J. Butler, et al., "The one-electron reduction potential of several substrates can be related to their reduction rates by cytochrome P-450 reductase" *Biochimica et Biophysica Acta* 1161: 73 (1993). A review of chemical potentials for electron couples detailing one-electron processes for reduction of oxidants (reduction of electron acceptor) and oxidation of reductants (oxidation of an electron donor) gives values for approximately 700 compounds (see, P. Wardman "Reduction Potentials of One-Electron Couples Involving Free Radicals in Aqueous Solution" *J. Phys. Chem. Ref Data* 18(4): 1637–1755 (1989) including flavin, bipyridinium, nitroaryl, phenol, terpenoid, imidazole, amine, peroxide and indole compounds. Iodosobenzene and N-oxide of p-cyano-N,N-dimethylalanine have been used for oxidation reactions with CYP in chemical models (see, W. Nee, et al., "Use of N-oxide of p-Cyano-N,N-dimethylalanine as an "Oxygen" Donor in a Cytochrome P-450 Model System" *J Am. Chem. Soc.* 104: 6123 (1982)), but they have not been applied to plants or other biological systems.

U.S. Pat. No. 5,532,204 proposes foliar applied methanol at the R5 seed growth stage of legumes. U.S. Pat. No. 5,300,540 proposes preservation of freeze-dried plant cells with barrier compositions containing, polyethylene glycol, p-aminobenzoic acid, acetylsalicylic acid, cinnamic acid, benzoic acid, blended alcohol and other organics. U.S. Pat. No. 3,897,241 proposes application of ethanolamine formulations with carboxylic acids of less than 8 carbons, such as, oxalic acid, formic acid, acetic acid, phthalic acid and glutaric acid to fruit-bearing plants. U. S. Pat. No. 4,799,953, proposes polymeric condensates of the sulfur-polymers of thiolactic and thioglycolic acids, increasing the rate of growth and production of chlorophyll specific to tissue and hydroponic culture of Lemna minor. European Patent 465 907 A1 proposes compositions for stimulating the growth and ripening of plants comprised of at least one adduct of menadione bisulfite and a compound chosen from a group including pABA, nicotinamide, nicotinic acid, thiamine, tryptophan, histidine, or adenine. U.K. Patent Application 2 004 856 proposes plant growth stimulating compositions consisting of cysteine as the active component in formulations that also include sulfosalicylic acid, folic acid, an aldehyde, a magnesium salt, and a buffer. European Patent FR 2 689 905 A1 proposes a method for cloning DNA sequences coding for an NADPH Cytochrome P450 reductase implicated by survival of a deficient mutant of *Saccharomyces cerevisiae*.

PCT WO94/00009 is the published text of parent application PCT/US93/05673 (published on Jan. 6, 1994) and U.S. Pat. No. 5,597,400 issued on Jan. 28, 1997. South African patent 93/4341, which is also the equivalent of PCT/US93/05673, issued on March 30, 1994. South African patent 96/1637, which is also the equivalent U.S. application Ser. No. 08/610,928, filed on Mar. 5, 1996, which was filed as a PCT International Application PCT/US96/02444, on Feb. 20, 1996.

SUMMARY OF THE INVENTION

As a first aspect, the present invention provides methods for treating plants. The methods include (a) applying to the plant a first compound selected from the group consisting of (i) NADPH:cytochrome P450 reductase enzyme and (ii) oxidants that induce NADPH:cytochrome P450 reductase in plants; and (b) applying to the plant a second compound selected from the group consisting of (i) cytochrome P450 monooxygenase enzyme and (ii) reductants that induce cytochrome P450 monooxygenase.

As a second aspect, the present invention provides a second method for treating a plant. The method comprises (a) applying to the plant an oxidant selected from the group consisting of flavins, salts of flavins, hydrates of flavins, surfactant-linked derivatives of flavins, and combinations thereof, and (b) applying to the plant a reductant that induces cytochrome P450 monooxygenase.

As a third aspect, the present invention provides a method for increasing the amount of cytochrome P450 in a photosynthetic plant. The method comprises (a) applying to the plant an oxidant that induces NADPH:cytochrome P450 reductase in plants, and (b) applying to the plant a reductant that induces cytochrome P450 monooxygenase. The oxidant is selected from the group consisting of flavins, salts of flavins, hydrates of flavins, surfactant-linked derivatives of flavins, and combinations thereof.

As a fourth aspect, the present invention provides a method for enhancing growth of a plant. The method comprises (a) applying to the plant an amount of an oxidant which induces NADPH:cytochrome P450 reductase in the plant, and (b) applying to the plant an amount of a reductant which induces cytochrome P450 monooxygenase in the plant. The oxidant is selected from the group consisting of flavins salts of flavins, hydrates of flavins, surfactant-linked derivatives of flavins, and combinations thereof.

As a fifth aspect, the present invention provides a plant growth enhancing system. The system comprises (a) an aqueous solution containing an amount of an oxidant which induces NADPH:cytochrome P450 reductase in the plant, and (b) an aqueous solution containing an amount of a reductant which induces cytochrome P450 monooxygenase in the plant. The oxidant is selected from the group consisting of flavins, salts of flavins, hydrates of flavins, surfactant-linked derivatives of flavins, and combinations thereof.

As a sixth aspect, the present invention provides a composition for enhancing growth of a plant. The composition comprises (a) an aqueous solution containing an amount of an oxidant which induces NADPH:cytochrome P450 reductase in the plant, and (b) an aqueous solution containing an amount of a reductant which induces cytochrome P450 monooxygenase in the plant. The oxidant is selected from the group consisting of flavins, salts of flavins, hydrates of flavins, surfactant-linked derivatives of flavins, and combinations thereof.

As a seventh aspect, the present invention provides a second composition for enhancing growth of a plant. The composition comprises (a) a first compound selected from the group consisting of (i) NADPH:cytochrome P450 reductase enzyme and (ii) oxidants that induce NADPH:cytochrome P450 reductase in plants; and (b) a second compound selected from the group consisting of tyrosine, tyrosine ester, and salts thereof.

As an eighth aspect, the present invention provides another method for enhancing growth of a plant. The method comprises applying to the foliage of a plant, a composition comprising (i) a reductant and (ii) an agronomically suitable surfactant. The reductant is selected from the group consisting of tyrosine, tyrosine ester, tyrosine methylester, and tyrosine methylester hydrochloride As a ninth aspect, the present invention provides yet another method for enhancing growth of a plant. The method comprises applying to the foliage of the plant, a composition comprising (i) a flavin and (ii) an agronomically suitable surfactant. The flavin is selected from the group consisting of flavin mononucleotide, flavin adenine dinucleotide, riboflavin, deazaflavin, salts thereof, hydrates thereof, surfactant-linked derivatives thereof, and combinations thereof.

These and other aspects of the present invention are described further in the detailed description and examples of the invention which follow.

DESCRIPTION OF THE PREFERRED EMBODIMENT

I. Definitions

Figure 1:
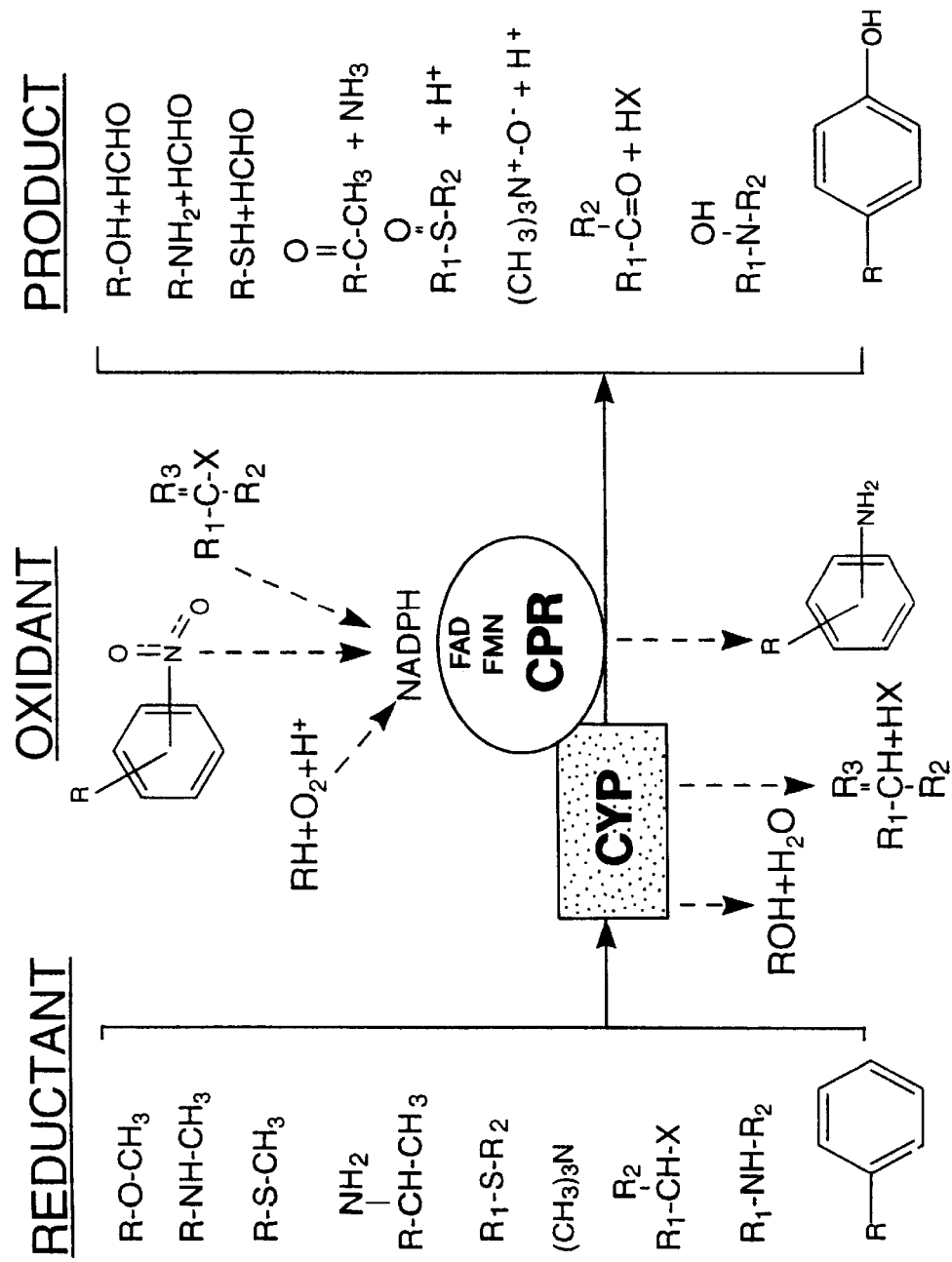
FIG. 1 is a simplified and general schematic depiction of the electron couple pairing to the catalytic cycle of cytochromes P450. Reductants are given in the left vertical column, which would function through CYP. Products of the oxygen insertion are given in the right vertical column. At the top center of the figure are examples of oxidants which function through flavin reductases such as CPR. Products are given at the bottom center of the figure. Improvement of plant growth is achieved by formulating CPR substrates with CYP inducers.

According to the present invention, methods, compositions, and systems are provided for coinducing cytochromes P450 monooxygenases (CYP) and NADPH:Cytochrome P450 reductases (CPR). Methods are provided for treating plants, particularly photosynthetic plants with the compositions of the present invention.

Unless otherwise defined, all technical and scientific terms employed herein have their conventional meaning in the art. As used herein, the following terms have the meanings ascribed to them.

"Oxidant" refers to electron acceptors or reductase substrates that induce CPR. Reductase substrates which induce CPR accelerate the metabolism of reductants by CYP.

"Reductant" refers to electron donors or oxidase substrates that induce CYP. Oxidase substrates which induce CYP accelerate the metabolism of oxidants by CPR.

"Enhance(s) growth" or "enhancing growth" refers to promoting, increasing or improving the rate of growth of the plant or increasing or promoting an increase in the size of the plant. Without wishing to be bound by any particular theory regarding the mechanism by which the compositions of the present invention enhance the growth of a plant, it is believed that when CYP and CPR enzymes are induced exogenously, they are enhanced beyond the natural content of a plant and, thereby lead to the enhanced growth of the plant. Enhancement of CYP and CPR increases the capacity of an organism to insert oxygen into metabolites and xenobiotics.

"Plants" refers to virtually all live species with active light-gathering surfaces capable of receiving treatments, particularly higher plants that fix carbon dioxide.

"Surfactant" refers to surface-active agents, i.e., which modify the nature of surfaces, often by reducing the surface tension of water. They act as wetting agents, spreaders, dispersants, or penetrants. Typical classes include cationic, anionic (e.g., alkylsulfates), nonionic (e.g., polyethylene oxides) and ampholytic. Soaps, alcohols, and fatty acids are other examples.

"Surfactant-linked derivative" refers to a derivative of the parent compound, the derivative having a surfactant covalently attached to the parent compound. A representative example of a parent compound and a surfactant-linked derivative thereof is p-aminobenzoic acid and its surfactant-linked derivative polyethoxylated p-aminobenzoic acid (Uvinul® P-25).

"Percent" or "%" is percent by weight unless otherwise indicated.

"ppm" refers to parts per million by weight.

"Alkyl" refers to linear, branched or cyclic; saturated or unsaturated $C_1$–$C_8$ hydrocarbons. Examples of alkyl groups include methyl, ethyl, ethenyl, propyl, propenyl, isopropyl, butyl, isobutyl, t-butyl, pentyl, hexyl, cyclohexyl, octyl, and the like.

"Aqueous" with reference to solutions or solvents refers to solutions or solvents which consist primarily of water, normally greater than 90 percent water, and can be essentially pure water in certain circumstances. For example, an aqueous solution or solvent can be distilled water, tap water, or the like. However, an aqueous solution or solvent can include water having substances such as pH buffers, pH adjusters, organic and inorganic salts, alcohols (e.g., ethanol), sugars, amino acids, or surfactants incorporated therein. The aqueous solution or solvent may also be a mixture of water and minor amounts of one or more cosolvents, including agronomically suitable organic cosolvents, which are miscible therewith, or may form an emulsion therewith. Agronomically suitable organic solvents include, for example, acetone, methanol, nitromethane, limonene, paraffin oils, siloxanes, esters, ethers, and emulsifiers.

The compositions and methods of the present invention may be applied to virtually any variety of plants. In particular, the compositions and methods of the present invention may be advantageously applied to "higher plants." Higher plants include, but are not limited to all species having true stems, roots, and leaves, thus excluding "lower plants" such as bacteria, yeasts and molds. Plants which may benefit according to the present invention include but are not limited to all crop plants, such as, alfalfa, anise, bach ciao, barley, basil, blueberry, breadfruit, broccoli, brussels sprouts, cabbage, cassava, cauliflower, celery, cereals, cilantro, coffee, corn, cotton, cranberry, cucumber, dill, eggplant, fennel, grape, grain, garlic, kale, leek, legume, lettuce, mint, mustard, melon, oat, onion, parsley, peanut, potato, saffron, millet, parsnip, pea, pepper, peppermint, pumpkin, radish, rice, sesame, sorghum, soy, spinach, squash, stevia, strawberry, sunflower, sweet potato, sugar beet, sugar cane, tea, tobacco, tomato, turnip, wheat, yam, zucchini and the like; pomes and other fruit-bearing plants, such as, apple, avocado, banana, breadfruit, cherry, citrus, cocoa, fig, guava, macadamia, mango, mangosteen, nut, olive, papaya, passion fruit, pear, pepper, plum, peach and the like; floral plants, such as achillea, ageratum, alyssum, anemone, aquilegia, aster, azalea, begonia, birds-of-paradise, bleeding heart, borage, bromeliad, bougainvillea, buddlea, cactus calendula, camellia, campanula, carex, carnation, celosia, chrysanthemum, clematis, cleome, coleus, cosmos, crocus, croton, cyclamen, dahlia, daffodil, daisy, day lily, delphinium, dianthus, digitalis, dusty miller, euonymus, forget-me-not, fremontia, fuchsia, gardenia, gazania, geranium, gerbera, gesneriad, ginkgo, gladiolus, hibiscus, hydrangea, impatiens, jasmine, lily, lilac, lisianthus, lobelia, marigold, mesembryanthemum, mimulus, myosotis, New Guinea Impatiens, nymphaea, oenothera, oleander, orchid, oxalis, pansy, penstemon, peony, petunia, poinsettia, polemonium, polygonum, poppy, portulaca, primula, ranunculus, rhododendron, rose, salvia, senecio, shooting star, snapdragon, solanum, solidago, stock, ti, torenia, tulip, verbena, vinca, viola, violet, zinnia, and the like; leafy plants, such as ficus, fern, hosta, philodendron, and the like; trees, such as Abies, birch, cedar, Cornus, cypress, elm, ficus, fir, juniper, magnolia, mahogany, maple, oak, palm, Picea, Pinus, Pittosporum, Plantago, poplar, redwood, Salix, sycamore, Taxus, teak, willow, yew, Christmas tree and the like; grasses, such as Kentucky blue grass, bent grass, turf, festuca, pennisetum, phalaris, calamogrostis, elymus, helictotrichon, imperata, molina, carex, miscanthus, panicum, and the like; and thalloid plants such as algae. This list is intended to be exemplary and is not intended to be exclusive. Other plants which may benefit by application of the compositions and methods of the present invention will be readily determined by those skilled in the art.

The methods and compositions of the present invention may be used to enhance growth in juvenile and mature plants, as well as cuttings and seeds. Generally, however, it is desirable that the plants include at least the sprouted cotyledon (i.e., the "seed leaves") or other substantial light-gathering surfaces including the true leaves.

As provided herein, enhancement of CYP and CPR focuses on modulating electron and oxygen transfer through CYP and CPR in a manner that shifts the flow of electrons in plants. FIG. 1 is a schematic depiction of the electron couple pairing to the catalytic cycle of cytochromes P450. By inducing or adding to the CYP and CPR of a leaf, the reductive capacity for growth is enhanced. An enhanced pool of CYP allows increased leaf capacity for electron transfer via CPR and vice versa. Accordingly, the compositions and methods of the present invention include, in general, an oxidant component and a reductant component.

II. Methods and Compositions

The present invention provides methods for treating plants, for increasing the amount of cytochrome P450 in a photosynthetic plant, and for enhancing the growth of a plant. These methods typically involve the application of an oxidant component and the application of a reductant component to the plant.

A. Oxidants

As noted above, oxidants are compounds which induce NADPH:cytochrome P450 reductase. Any compound capable of inducing such reductase will be useful as the oxidant component in the methods, compositions, and systems of the present invention. Accordingly, reductases, particularly CPR, may be utilized as the oxidant component of the methods, compositions, and systems of the present invention. In addition, a number of other suitable oxidants will be readily determinable by those skilled in the art.

Preferred oxidant compounds exhibit a one electron reduction potential ($E_0$) between about $-400$ mV and about $-165$ mV inclusive, more preferably between about $-396$ mV and about $-240$ mV. Some multiple electron reductions are also biologically important with CYP and oxygen. Examples of suitable reductants include but are not limited to ferredoxin-NADP$^+$ reductases, including the reductases listed hereinabove as well as, flavins, nitrobenzoate compounds, nicotinic acids, nitrobenzoic acid compounds, haloaryl compounds, amine oxides, formamidines, glycolates and glycolic metabolites, cytochrome reductases, azo compounds, quinone compounds, bipyridinium compounds, and all salts, hydrates, aldehydes, esters, amines, surfactant-linked derivativates, and other biologically or chemically equivalent derivatives thereof and combinations thereof.

Specific examples of flavins which are useful as oxidants in the methods and compositions of the present invention include but are not limited to flavin mononucleotide (FMN), flavin adenine dinucleotide (FAD), deazaflavin, riboflavin, lumichrome, lumizine, alloxazine, salts of any of the foregoing flavins, hydrates of any of the foregoing flavins, surfactant-linked derivatives of any of the foregoing flavins, and combinations thereof.

Specific examples of nitrobenzoate compounds include but are not limited to p-nitrobenzoate, polyethylene glycol nitrobenzoate, and combinations thereof.

Specific examples of nitrobenzoic acid compounds include but are not limited to m-nitrobenzoic acid, p-nitrobenzoic acid (pNBA), 4-chloro-2-nitrobenzoic acid, 2-chloro-4-nitrobenzoic acid, p-nitrophenol, nitrophenolates, salts thereof, hydrates thereof, and combinations thereof.

Specific examples of haloaryl compounds include but are not limited to iodobenzoic acid, iodosobenzene, and combinations thereof.

Specific examples of amine oxides include but are not limited to tertiary amine-N-oxide, N,N-dimethylhexadecylamine N-oxide, N,N-dimethylisooctadecaneamine N-oxide, N,N-dimethyloctadecylamine N-oxide, N,N-dimethyloctylamine N-oxide, N,N-dimethyltetradecylamine N-oxide, cocoamide N-(3-dimethylamino) propyl N-oxide, $C_6$–$C_{24}$ alkyl dimethylamine N-oxide, bis (2-hydroxyethyl)-3-(decycloxy) propylamine N-oxide, cocoalkyldimethylamino N-oxide, and combinations thereof.

Specific examples of formamidines include but are not limited to formamidine acetate, formamidine hydrochloride, formamidine glycolate, formamidine formate, formamidine sulfuric acid, forniminoglutamate, formiminoglycine, and combinations thereof.

Specific examples of glycolates and glycolic metabolites include but are not limited to glycolate, potassium glycolate, glycolic acid, formate, oxalate, $C_1$-tetrahydrofolate, salts thereof, hydrates thereof, and combinations thereof.

Specific examples of cytochrome reductases include but are not limited to cytochrome f, cytochrome c, cytochrome b5, flavocytochrome P450, nitric oxide synthase, and combinations thereof.

Specific examples of azo compounds include but are not limited to azo dyes, azodicarboxamide, diazolidinylurea, and combinations thereof.

Specific examples of nicotinic acids include but are not limited to niacin, NAD, NADP, and combinations thereof.

Specific examples of quinone compounds include but are not limited to anthraquinone sulfonate, 1,4-bis[(2-ethylhexyl)amino]anthraquinone, tert-butyl hydroquinone, and combinations thereof Specific examples of bipyridinium compounds include but are not limited to bis(dimethylaminocarbonyl) propylbipyridinium, ethylpropenylmethoxyethylbipyridinium and combinations thereof.

Compounds selected from the aforementioned classes based solely upon optimal $E_0$ values would, for example, include anthraquinone sulfonate (−390 mV), bis (dimethylaminocarbonyl)propylbipyridinium (−399 mV), ethylpropenylmethoxyethylbipyridinium (−396 mV), the oxygen radical (−330 ), all of which are operational in the present invention, but may be impractical due to cost. Examples of preferred oxidants whose selection is based on $E_0$ values and beneficial metabolism include p-nitrobenzoic acid (−396 mV), glycolic acid (−290 mV), riboflavin (−292 mV), FMN (−313 mV), FAD (−241 mV) and salts, hydrates and surfactant-linked derivatives of any of the above.

Currently preferred oxidants for use in the methods and compositions of the present invention include but are not limited to FAD, FMN, pNBA, p-nitrophenolate, glycolate, and salts, hydrates and surfactant-linked derivatives thereof. FMN is a particularly preferred oxidant in the compositions, methods and systems of the present invention, primarily because it is cost effective.

As noted above, the oxidant employed in the present invention may comprise any two or more of the foregoing oxidants in combination. For example, in one preferred embodiment, the oxidant comprises a combination of FMN and FAD. In the embodiment of the invention wherein two or more oxidants are combined, the two or more oxidants are typically provided in equimolar quantities to provide the oxidant component of the compositions and methods of the present invention.

B. Reductants

Reductants are compounds which induce cytochrome P450 monooxygenase. Any compound capable of inducing such enzyme will be useful as the reductant component in the present invention. The reductant is usually selected from the group consisting of components that are capable of accepting activated oxygen from metalloporphyrins. Reductants can be hydroxylated, dealkylated, oxidatively deaminated, sulfoxidized, oxidized, peroxidized, epoxidized and oxidatively dehalogenated by CYP.

Preferred reductants include, but are not limited to those electron donors with a reduction potential ($E_0$) between about 1 and about 2000 mV, and more preferably between about 600 mV and about 900 mV. Examples of suitable reductants include but are not limited to cytochromes, peroxisome proliferators, amines, cinnamates, retinoids, fatty acids, carbamates, manganese, pteridines, terpenoids, alcohols, ketones, pyridines, indoles, brassinolides, barbiturates, flavones, salts of any of the foregoing, esters of any of the foregoing, phosphates of any of the foregoing, hydrates of any of the foregoing, surfactant-linked derivatives of the foregoing, and combinations thereof. Plant metabolites are also suitable reductants.

Specific examples of cytochromes which may be employed as reductants in the methods of the present invention include but are not limited to, hemoglobin, human CYP, insect CYP, animal CYP, fungal CYP, plant CYP, bacterial cytochromes, viral cytochromes, microsomes, salts, hydrates, and surfactant-linked derivatives thereof, and combinations thereof.

Specific examples of peroxisome proliferators which may be employed as reductants in the methods of the present invention include but are not limited to dihydroxytetraeicosatrienoic acid, thiazolidinedinone-4-carboxylic acid, and pimelic acid.

Specific examples of amines which may be employed as reductants in the methods of the present invention include but are not limited to tyrosine, tyrosine ester, N-acetyltyrosine, tyrosine methylester, tyrosine methylester hydrochloride, tyramine, alanyltyrosine, levodopa, aminopyrine, phosphonomethylglycine, and combinations thereof.

Specific examples of terpenoids which may be employed as reductants include but are not limited to cinnamates such as trans-cinnamic acid; orcinols such as resorcinol; and hydroxybenzoates such as salicylates and aspirin; and combinations thereof.

A specific example of a retinoid which may be employed as a reductant is trans-retinoic acid.

Specific examples of fatty acids which may be employed as reductants include but are not limited to lauric acid, palmitic acid, arachidonic acids, linoleic acid, and combinations thereof.

Specific examples of alcohols which may be employed as reductants include but are not limited to alkanols such as methanol, ethanol, phenol, alcohol amines such as triethanolamine, and combinations thereof.

A specific ketone which may be employed as a reductant is acetone.

Specific examples of pyridines which may be employed as reductants include pyridine, and alkyl substituted pyridines.

Specific examples of pteridines which may be employed as reductants include but are not limited to aminobenzoic acids such as m-aminobenzoic acid, p-aminobenzoic acid, PEG-25 p-aminobenzoic acid; tetrahydrofolates such as tetrahydrobiopterin; and combinations thereof.

Specific examples of carbamates which may be employed as reductants include but are not limited to N-(3,4-methylenedioxyphenyl)carbamates, 3-iodo-2-propynylbutylcarbamate, ammonium carbamate, o-chlorophenyl N-methylcarbamate, and combinations thereof.

Specific examples of indoles which may be employed as reductants include indole-3-glycerol phosphate, indole-3-acetic acid, indole-3-butyric acid, and combinations thereof.

Specific examples of barbiturates which may be employed as reductants include phenobarbital and hexobarbital.

A specific flavone which may be employed as the reductant is isoflavone.

Preferred reductants include various forms of tyrosine such as tyrosine (640 mV), N-acetyltyrosinamide (650 mV), alanyltyrosine (850 mV), tyrosine methylester (870 mV); tyrosine methylester hydrochloride; amines, particularly aminopyrine; pteridines, particularly p-aminobenzoic acid, and PEG-25 p-aminobenzoic acid; and hydroxybenzoic acids (>500 mV).

Compounds that inhibit cytochromes P450 are not generally useful in the compositions, methods and systems of the present invention. These compounds include compounds that accelerate degradation or that bind to the heme iron atom or to the prosthetic heme group. Unsuitable compounds include in general carbon monoxide, carbon tetrachloride, cyanide, cimetidine, allylisopropylacetamide, piperonyl butoxide, 1-[4-(3-acetyl -2,4,6-trimethylphenyl)-2,6-cyclohexanedionyl]-O-ethyl propionaldehyde oxime, hydrogen peroxide, cumene hydroperoxide, phenylimidazole, aminoglutethimide, terconazole, fluconazole, saperconazole, miconazole, metyrapone, ketoconazole, parathion, carbon disulfide, thiourea, tienilic acid, diethyldithiocarbamate, isothiocyanate, mercaptosteroid, chloramphenicol, dichloroacetamides, undecynoic acid, ethynylpyrene, ethynylprogesterone, ethynylnaphthalene, secobarbital, dihydropyridine, dihydroquinoline, 1,1-disubstituted hydrazine, acyl hydrazine, alkyl hydrazine, aryl hydrazine, phenelzine, aminobenzotriazole; syndones, 2,3-bis(carbethoxy)-2,3-diazabicyclo[2.2.0]hex-5-ene, and phenylphenanthridinone.

C. Application

Certain of the oxidants and reductants are, by themselves useful in methods of treating plants and in methods of enhancing the growth of plants. For example, the flavins, by themselves, or together with an agronomically suitable additive may be useful in the methods of the present invention without the additional application of a reductant. As another example, tyrosine and tyrosine esters such as tyrosine methylester and tyrosine methylester hydrochloride are useful by themselves or together with an agronomically suitable additive in the methods of the present invention without the additional application of an oxidant.

Typically, however, the oxidant component and the reductant component are co-applied to achieve beneficial results in methods of treating plants, enhancing growth, and increasing cytochrome P450 in photosynthetic plants. The co-application of an oxidant and a reductant does not require the simultaneous application of these components. The methods of the present invention include the simultaneous application of the oxidant and reductant from separate sources, the separate application of the oxidant and reductant wherein the oxidant is applied first followed by the application of the reductant, and the separate application of the oxidant and the reductant wherein the reductant is applied first followed by the application of the oxidant. When the oxidant and reductant are separately applied, they are typically applied at or near the same time, and generally one is applied within a 24 hour period of the other, preferably within a 12 hour period, more preferably within a 3 hour period and most preferably within a 1 hour period. In addition, the oxidant and the reductant may be formulated into a single composition and thereby simultaneously applied to the plant.

Although the oxidant and reductant components may be applied in a solid form, it is often advantageous to provide the oxidant and the reductant in liquid form, such as by solubilizing the component in an aqueous or agronomically suitable organic solvent or carrier to produce aqueous or organic solutions of the oxidant and/or reductant for application to the plant. The amount of oxidant which is solubilized in the carrier will depend upon the particular oxidant selected and the method of application. The oxidant may be solubilized in the carrier by adding the oxidant to the carrier and allowing the oxidant to dissolve. In some instances, the application of stirring, agitation, or even heat may facilitate the dissolution of the oxidant in the carrier.

Typically, the oxidant is applied as an aqueous solution having an oxidant concentration in the range between about 0.0001% and about 1% by weight of the composition inclusive, preferably between about 0.01% and about 0.5% inclusive. For example, a flavin mixture of FAD:FMN at a ratio of 829:456 is preferred to match equimolar ratios generally found in CPR and will range from 8 ppm:5 ppm to 829 ppm:456 ppm. For glycolate, preferably from about 0.2% to 0.8% glycolate solutions are suitable for germlings; and from about 0.5% to 5% glycolate solutions are suitable for mature crop plants, more preferably from about 0.3% to 0.6% potassium glycolate solutions are used for open field crops. For pNBA, preferably from about 50 ppm to 300 ppm pNBA solutions are suitable for seedlings and from about 150 ppm to 900 ppm pNBA solutions are suitable for mature crop plants, more preferably from about 600 ppm to 800 ppm pNBA solutions are suitable for open field crops of strawberries.

Similarly, the amount of reductant which is solubilized in the carrier will depend upon the particular reductant selected and the method of application. The reductant may be solubilized in the carrier by adding the reductant to the carrier and allowing the reductant to dissolve. In some instances, the application of stirring, agitation, or even heat may facilitate the dissolution of the reductant in the carrier. Typically, the reductant is applied as an aqueous solution having a reductant concentration in the range between about 0.0001% and about 10% by weight of the composition inclusive, preferably between about 0.01% and about 0.3% inclusive. In one preferred embodiment, the reductant is provided at or below a concentration of about 0.1%, more preferably at about 0.05%. For example, salicylates are typically provided in carrier solutions at a concentration of from about 50 ppm to about 200 ppm by weight for seedlings and sensitive plants and more preferably about 300 ppm to 900 ppm for open field crops. Tyrosines are preferably provided in an aqueous solution at a concentration from about 600 ppm to 2000 ppm for seedlings and sensitive plants and more preferably from about 900 ppm to 9000 ppm for open field crops.

In the embodiment wherein the oxidant and the reductant are combined into a single composition for use in the methods of the present invention, the composition includes an aqueous or agronomically suitable organic solution having solubilized, dispersed, or otherwise contained therein, an amount of the oxidant that induces NADPH:cytochrome P450 reductase in the plant, and an aqueous solution having solubilized dispersed or otherwise contained therein, an amount of the reductant that induces cytochrome P450 monooxygenase in the plant. The solution containing the oxidant and reductant may be prepared using the general techniques set forth above for solubilizing oxidant or reductant alone.

Compositions containing both the oxidant and the reductant are advantageous in that they permit the one-step application of both components to the plant. The one-step compositions of the invention will comprise an aqueous solution or agronomically suitable organic solvent emulsion of one or more reductants in combination with one or more oxidants. Typically, the amount of reductant present is sufficient to balance the amount of oxidant present, in terms of electron transfer potential, when both are applied to the plant. The preferred oxidant:reductant molar ratio will be in the broad range of from about 10:1 to about 1:2, preferably from about 3:1 to about 1:1.

Compositions containing both the oxidant and the reductant component in a single solution may include any combination of oxidants and reductants selected from those described hereinabove. Preferred oxidants for one-step compositions include, but are not limited to glycolates, FAD, FMN and pNBA. Preferred reductants for one-step compositions include, but are not limited to, alcohols, aminopyrine, aspirin, p-aminobenzoic acid, orcinol, levodopa, trans-retinoic acid, tyrosine, and tyrosine esters including tyrosine methylester and tyrosine methylester hydrochloride. For example, one composition according to the present invention includes glycolate and tyrosine methylester. Another composition according to the present invention includes glycolate and alanyltyrosine. Another composition according to the present invention includes riboflavin and aspirin. Another composition according to the present invention includes pNBA and aminopyrine.

Compositions of oxidants with reductants will typically be applied at a concentration ranging between about 0.0001% and about 10%. Preferred combined oxidant and reductant compositions include: (1) pNBA and aminopyrine applied as an aqueous solution, each at a concentration in the range of from about 0.001% to about 1%; (2) FAD:FMN and retinoic acid applied as an aqueous solution each at a concentration in the range of from about 0.001% to about 0.1%; (3) glycolate and tyrosine methyl ester hydrochloride applied each at a concentration in the range from about 0.01% to about 5%; and (4) potassium glycolate applied as an aqueous solution each at a concentration in the range from about 1000 ppm to about 8000 ppm in combination with salicylate in the range from about 50 ppm to about 900 ppm.

While the compositions of the present invention may consist essentially of the aqueous solutions of oxidant and reductant, oil soluble compounds may be formulated in agronomically suitable organic solvents. For example, 2-methyl-1,4-naphthalenedione and naphthalic anhydride may be formulated as concentrates with paraffin oil as the carrier for application in appropriate crop emulsions, hydrosols or organic films.

The compositions of the present invention may also include any of a wide variety of agronomically suitable additives, adjuvants, or other ingredients and components which improve or at least do not hinder the beneficial effects of the compositions of the present invention (hereinafter "additives"). Generally accepted additives for agricultural application are periodically listed by the United States Environmental Protection Agency. For example, foliar compositions may contain a surfactant and a spreader present in an amount sufficient to promote wetting, emulsification, even distribution and penetration of the active substances. Spreaders are typically organic alkanes, alkenes or polydimethylsiloxanes which provide a sheeting action of the treatment across the phylloplane. Suitable spreaders include paraffin oils and polyalkyleneoxide polydimethylsiloxanes. Suitable surfactants include anionic, cationic, nonionic, and zwitterionic detergents, amine ethoxylates, alkyl phenol ethoxylates, phosphate esters, PEG, polymerics, polyoxyethylene fatty acid esters, polyoxyethylene fatty diglycerides, sorbitan fatty acid esters, alcohol ethoxylates, sorbitan fatty acid ester ethoxylates, ethoxylated alkylamines, quaternary amines, sorbitan ethoxylate esters, alkyl polysaccharides, block copolymers, random copolymers, trisiloxanes, CHELACTANTS™ and blends. Surfactant preference is for polyalkylene oxides, polyalkylene glycols, and alkoxylate-fatty acids. Blends are highly effective such as our organosiloxane/nonionic surfactant SILWET® Y14242 (Y14242) blend which use is demonstrated in our examples. Preferred commercial aqueous surfactants include Hampshire LED3A; HAMPOSYL®; TEEPOL®; TWEEN®; TRITON®; LATRON™; PLURONIC®; TETRONIC®; SURFONIC®; SYNPERONIC®; ADMOX®; DAWN®, and the like. Commercial emulsifiers for combination with organic solvent formulations include WITCANOL®, RHODASURF®, TERGITOL® and TWEEN®. Commercial spreaders include TEGOPREN®, AGRIMAX™, DOW CORNING® 211, X-77®, SILWET® and the like. Penetrants such as sodium dodecylsulfate, formamides and lower aliphatic alcohols, may be used. Alkoxylation of an active component or otherwise chemically modifying the active components by incorporating a penetrant substance is useful because formulation without additional surfactant is achieved.

Macromolecules such as CPR and CYP pose problems related to cellular penetration. Addition of diatomaceous earth, carborundum, fine sand or alumina may be added to the compositions of the present invention to scratch the leaf surface and assist with penetration of macromolecules. Small quantities (0.03–0.3%) of sterile diatomaceous earth are preferred additions to the adjuvant formulation to enhance penetration of macromolecules. In some cases such as cabbage, in which cells are tough, gentle movement of the diatoms across the leaf surface by mechanical rubbing or high pressure treatments may be applied.

In addition to the foregoing additives, the compositions of the present invention may also advantageously include one or more fertilizers. Suitable fertilizers for inclusion in the compositions, methods and systems of the present invention will be readily determninable by those skilled in the art and include conventional fertilizers containing elements such as nitrogen, phosphorus, potassium, elevated carbon dioxide, hydrogen peroxide and the like. Nitrogenous fertilizers (i.e., fertilizers containing nitrogen) are currently preferred; particularly nitrogenous fertilizers containing not more than 1.5% ammoniacal nitrogen (i.e., nitrogen in the form of ammonia or ammonium ion), preferably not more than 1.2% ammoniacal nitrogen, more preferably less than 1% ammoniacal nitrogen. Nitrate fertilizers (containing less than 1.5% ammoniacal nitrogen) are preferred fertilizers for inclusion in the methods of the present invention. In particular, in cases requiring foliar fertilizers, nitrate fertilizers are preferred. Low concentrations of ammonia fertilizers may be fed to plants at least 2 days after treatment, preferably through the roots. The amount of fertilizer added to the compositions of the present invention will depend upon the plants to be treated, and the nutrient content of the soil. Typically, the conventional fertilizer is included in the amount of between about 1 ppm and about 1000 ppm, preferably between about 10 ppm and about 400 ppm, and more preferably between about 25 ppm and about 50 ppm by weight of the composition.

In addition to the conventional fertilizers, the compositions of the present invention may also include the novel $C_1$–$C_7$ alkyl glucoside fertilizers which are the subject of copending application Ser. No. 08/928,068, Attorney docket number 15190-000700 filed concurrently herewith in the name of the presently named inventors, the disclosure of which is incorporated herein by reference in its entirety. Preferred $C_1$–$C_7$ alkyl glucosides include methyl glucosides, particularly α-methyl glucoside and β-methyl glucoside; ethyl glucoside, propyl glucoside, and combinations thereof. Currently, the preferred alkyl glucosides for inclusion in the compositions, methods, and systems of the present invention are the α-methyl glucoside, β-methyl glucoside, and combinations thereof. As with conventional fertilizers, the amount of alkyl glucoside fertilizer included in the compositions of the present invention will depend upon the plants to be treated, and the nutrient content of the soil. Typically, the alkyl glucoside is included in the amount of between about 0.1% and about 10.0%, preferably between about 0.5% and about 5.0%, and more preferably between about 0.6% and about 2.0%.

The compositions of the present invention may also include any of various secondary nutrients, such as sources of sulfur, calcium, and magnesium; as well as micronutrients, such as chelated iron, boron, cobalt, copper, manganese, molybdenum, zinc, nickel, and the like, which are conventionally formulated in foliar fertilizers. Other conventional fertilizer constituents which may be added to the compositions of the present invention include pesticides, fungicides, antibiotics, plant growth regulators, gene therapies and the like.

The compositions of the present invention may be applied to the plants using conventional application techniques. Plants nearing or at maturity may be treated at any time before and during seed development. Fruit bearing plants may be treated before and after the onset of bud or fruit formation. Improved growth occurs as a result of inducing CYP and CPR.

The compositions of the present invention may be applied to the plant at a location including leaves, shoots, root, seed, and stem. The compositions may be applied to the leaves, seed or stem by spraying the leaves with the composition. The composition may be applied to the shoot or root by spraying the shoot or root, or dipping the shoot or root in a bath of the composition, or drenching the soil in which the plant is being cultivated with the composition, or spray-drenching the leaves and stem of the plant such that the soil in which the plant is being cultivated becomes saturated with the composition. Side dressing is also applicable.

Foliar application (i.e., application of the composition to one or more leaves of the plant) of the compositions of the present invention are currently preferred. The composition will normally be applied to the leaves of the plant using a spray. However, other means of foliar application such as dipping, brushing, wicking, misting, electrostatic dispersion and the like of liquids, foams, gels and other formulations may also be employed. Foliar sprays can be applied to the leaves of the plant using commercially available spray systems, such as those intended for the application of foliar fertilizers, pesticides, and the like, and available from commercial vendors such as FMC Corporation, John Deere, Valmont and Spraying Systems (TEEJET®). If desired, oxidant and reductant compounds may be applied to plants in rapid sequence from separate nozzles in separate reservoirs. Chemically compatible combined mixtures may be preferred for many applications to produce improved plant growth. High foliar content of CYP and CPR maintains high rates of growth during day and night, with greatest response when plants are exposed to water stress, warmth and high light intensity consistent with prolonged photorespiration. High potency is achieved by foliar application of compositions containing oxidant in combination with reductant or readily metabolized precursors, thereto. For example, the oxidant pNBA is formulated with the reductant aminopyrine; or the oxidant 5'-deazaflavin may be formulated with the reductant levadopa.

In the embodiment wherein the root and/or shoot is dipped in a bath of the composition, it is preferred to pulse the application of the composition of the present invention by dipping the shoot and/or root in the bath containing the composition for a period of time and then removing the shoot and/or root from the composition. The dipping period may be from 1 minute to 30 minutes, and is preferably from 10 to 15 minutes.

The compositions of the present invention may also be applied to plant tissues, such as cell suspensions, callus tissue cultures, and micropropagation cultures. Such plant tissues may be treated with the compositions of the present invention by adding the composition to the culture medium in which the plant tissues are being cultivated.

In the methods of the present invention, the compositions are typically applied in the amount of between about 3 gallons per acre and about 200 gallons per acre, depending upon the application method. For horticultural applications, the compositions are preferably applied in the amount of between about 75 gallons per acre and about 125 gallons per acre. For ground rig row crop applications, the compositions are preferably applied in the amount of between about 10 gallons per acre and about 40 gallons per acre. For aerial applications by helicopter or airplane crop dusters, the compositions are preferably applied in the amount of between about 1 gallon per acre and about 5 gallons per acre. The compositions may be applied in a single application, or in multiple applications interrupted by a period of photosynthetic activity. Ornamentals and other tender nursery plants meant for indoor horticulture will frequently require lower concentrations and perhaps more frequent application than outdoor agricultural crops.

In general agricultural practice, withholding fertilization of the crop for 2 days prior to and following treatment with crop enhancers is recommended to prevent interference. Suitable light and temperature conditions may be achieved by treating plants within 4 hours of sunrise. Optimal to hot temperatures, usually above 15° C. and preferably above 30° C., are required after treatment. The plants should remain exposed to the sunlight or high intensity illumination for a period of time sufficient to allow for incorporation of treatments. Usually, the plants should remain exposed to sunlight or other illumination during daylight photoperiods for at least three hours after treatments. Sufficient nutrients should be present to support healthy growth.

Throughout the growing season after treatments, either sun or artificial illumination should have an intensity and duration sufficient for prolonged high rates of photosynthesis. A minimum suitable illumination intensity is 200 μmol photosynthetically active quanta (400–700 nm) m$^{-2}$s$^{-1}$, with direct sunlight normally providing much higher illumination. Prior to treatment, leaf temperature should be sufficiently high for optimal growth or hotter, usually about 10° C. to 35° C. After treatment, the leaf temperature will normally drop as a consequence of improved photosynthetic efficiency. It is preferable that the plant be exposed to at least a week of intense illumination preferably greater than 500 μmol photosynthetically active quanta m$^{-2}$s$^{-1}$ following application of the compositions of the present invention.

Compositions according to the present invention may be tailored for specific uses, including enhanced performance or tolerance under environmental stress; enhanced yield; elongation of growing seasons; aftermarket caretaking; flower retention; fruit optimization; safening of xenobiotics; and in all areas of agriculture in which optimal growth is beneficial. Compositions may also be formulated at very low concentrations without surfactant or spreader for treatments of roots and liquid suspension culture media.

III. Systems

In addition to the methods and compositions described hereinabove, the present invention also includes a plant growth enhancing system. The system includes (a) an aqueous solution containing an amount of an oxidant which induces NADPH:cytochrome P450 reductase in the plant, and (b) an aqueous solution containing an amount of a reductant which induces cytochrome P450 monooxygenase in said plant. Typically, the oxidant is selected from the group consisting of flavins, salts of flavins, hydrates of flavins, surfactant-linked derivatives of flavins, and combinations thereof, although any of the oxidants described hereinabove may be employed in the systems of the present invention. The reductants employed in the systems of the present invention may also be selected from those described hereinabove. Preferred reductants for use in the systems of the present invention include but are not limited to hemoglobin, tyrosine, tyrosine ester, tyrosine methylester, tyrosine methylester hydrochloride, N-acetyl tyrosine, tyramine, alanyltyrosine, levodopa, aminopyrine, salicylates, orcinol, trans-retinoic acid, lauric acid, palmitic acid, m-aminobenzoic acid, p-aminobenzoic acid, PEG-25 p-aminobenzoic acid, indole-3-glycerol phosphate, indole-3-acetic acid, methanol, acetone, pyridine, manganese, tetrahydrobiopterin, phenobarbital, and combinations thereof. The aqueous solutions employed in the systems of the present invention may be formulated in the same manner as described hereinabove for compositions, using the same types of aqueous carriers. One preferred system according to the present invention includes flavin mononucleotide as the oxidant and p-aminobenzoic acid as the reductant. Another preferred system according to the present invention includes flavin mononucleotide as the oxidant and PEG-25 p-aminobenzoic acid as the reductant. Another preferred system according to the present invention includes flavin mononucleotide as the oxidant and tyrosine methylester (e.g., tyrosine methylester hydrochloride) as the reductant.

The following examples are provided to further illustrate the present invention, and should not be construed as limiting thereof. The present invention is defined by the claims which follow. In these examples, glycine (gly), HAMPOSYL® C, 50% potassium glycolate (GO), 45% potassium hydroxide (KOH), chelated manganese LED3A, and purified water were obtained from Hampshire Chemical Corporation.

Human Cytochrome P450 (CYP 2E1) and Human NADPH:Cytochrome P450 Reductase (Human CPR) were obtained from PanVera Corporation.

N-acetyltyrosinamide (NATA), alanyltyrosine (AlaTyr) aminopyrine (AP), ascorbic acid, CELITE®, ethanol (Ethan), glycerol, levadopa, potassium chloride (KCl), potassium cyanide (KCN), methanol (MeOH), polyvinylpolypyrrolidone (PVPP), potassium phosphate, sodium bicarbonate, and L-tyrosine (Tyr) were obtained from Fisher Scientific. N-acetyltyrosine (NAT), adenosine triphosphate (ATP), amino-n-caproic acid, aprotinin, benzamidine HCl, 7-benzyloxyresorufin (7B), bovine serum albumin (BSA), trans-cinnamic acid (cinnamic), cytochrome c, dithiothreitol (DTT), ethylenediamine tetraacetic acid (EDTA), ethylene glycol-bis(β-aminoethyl ether) (EGTA), flavin adenine dinucleotide (FAD), formaldehyde, formamidine acetate (FAM), formic acid, HEPES, leucovorin, leupeptin, magnesium chloride (MgCl$_2$), nitromethane (NM), nicotinamide adenine dinucleotide phosphate (NADP), orcinol monohydrate (OR), 4-aminobenzoic acid (PABA), pepstatin, potassium maleic acid (malate), pteroic acid (pteroic), trans-retinoic acid (RET), riboflavin (B$_2$), salicylic acid (sali), triethanolamine, TRITON® X-100, tyrosine methyl ester HCl (TyCIMe), and valine (Val) were obtained from Sigma.

4-Nitrobenzoic acid (pNBA) was obtained from Nordic Synthesis.

Ethoxylated PABA (UVINUL® P-25) and PLURONIC® L-92 were obtained from BASF.

$^{14}CO_2$ was obtained from ICN.

SYNPERONIC® and TWEEN® were obtained from ICI.

Flavin mononucleotide sodium salt (FMN) was obtained from Roche Vitamins Inc.

SILWET® Y14242 and 408, OSi; ADMOX® 10, 12, 14, Albemarle; iodosobenzene (10) were obtained from TCI.

AGSOLEX® 1 was obtained from ISP.

In these examples, "L" means liter; "ml" means milliliter; "cm" means centimeter; "cm$^2$" means centimeters squared; "mn" means nanometer; "g" means grams; "mg" means milligrams; "M" means molar; "mM" means millimolar; "nM" means nanomolar; "μM" means micromolar; "mol" means moles; "μmol" means micromoles; "mg/ml" means milligrams per milliliter; "ml/cm$^2$" means milliliters per centimeter squared; "ppm" means parts per million based on weight; "%" or "percent" means percent by weight (of the composition); "kDa" means kiloDaltons; "d" means day; "h" means hour(s); "min" means minute(s); "s" means second(s); "Xg" means multiple of centrifugal gravitational force; "° C." means degrees Centigrade (all temperatures are in ° C., unless otherwise indicated).

EXAMPLE 1

Following are examples of specific compositions according to the present invention which may advantageously be employed in the methods of the present invention to treat plants and to enhance growth in plants by increasing cytochrome P450 in plants. The following exemplary compositions are intended to provide further guidance to those skilled in the art, and do not represent an exhaustive listing of compositions within the scope of the present invention.

| First Exemplary Composition: Foliar | | |
|---|---|---|
| | Concentration | |
| Composition | Broad Range | Narrow Range |
| FMN | 100–500 ppm | 200–400 ppm |
| K-PABA | 50–1000 ppm | 200–500 ppm |
| Surfactants | 50–5000 ppm | 300–3000 ppm |

Second Exemplary Composition: Foliar

| Composition | Concentration Broad Range | Narrow Range |
|---|---|---|
| p-Nitrobenzoic acid (e.g. K salt) | 1–2000 ppm | 150–800 ppm |
| Aminopyrine | 1–1000 ppm | 50–500 ppm |
| Surfactants | 50–5000 ppm | 300–3000 ppm |

Third Exemplary Composition: Foliar

| Component | Concentration Broad Range | Narrow Range |
|---|---|---|
| p-Nitrobenzoic acid (e.g. K salt) | 1–2000 ppm | 150–800 ppm |
| trans-Cinnamic acid | 200–2000 ppm | 600–1000 ppm |
| Surfactants/Spreaders | 0.1% to 3% | 0.1% to 0.2% |

Fourth Exemplary Composition: Foliar

| Composition | Concentration Broad Range | Narrow Range |
|---|---|---|
| Glycolate (e.g. Mg salt) | 0.01% to 1% | 0.3% to 0.5% |
| FMN | 100–5000 ppm | 250–1000 ppm |
| Surfactants | 50–5000 ppm | 500–3000 ppm |

Fifth Exemplary Composition: Foliar

| Component | Grams | Range |
|---|---|---|
| FMN | 17.34 | 0.5–2X |
| Uvinul ® P-25 | 96.14 | 0.5–3X |
| Surfactant (dry powder) | 100 | 0.5–3X |

The slurry is warmed to 40° C. and stirred into 20° C. to 40° C. water to a final volume of 76 liters. The solution is adjusted within a range of pH 6 to pH 7 with suitable buffer. Addition of a spreader is recommended prior to application. The solution is sprayed on foliage or may be applied to any plant part.

Sixth Exemplary Composition: Dry Powder

| Component | Grams | Range |
|---|---|---|
| Tyrosine methyl ester HCl | 139 | 0.5–2X |
| Potassium glycolate | 575 | 0.5–3X |
| Surfactant (dry powder) | 100 | 0.5–3X |

The homogenous dry powder is stirred into tap water at about room temperature to a final volume of 100 liters. The solution is adjusted within a range of pH 5 to pH 7 as needed with base or suitable buffer. Addition of a spreader is recommended prior to application. The solution is sprayed on foliage or may be applied to any plant part.

EXAMPLE 2

The following example illustrates the application of numerous compositions according to the present invention to many varieties of plants. The data demonstrate the efficacy of the methods and compositions of the present invention in the treatment of plants.

Materials and Method

Plants tested under controlled and greenhouse conditions for growth response included radish cv Cherry Bell, pepper cv Bell Boy, wheat cv Geneva, pansy cv Delta Pure White, impatiens cv Super Elfin Violet and corn cv Butter Sugar. Gas exchange and metabolic analyses were undertaken on soy (Glycine max cv Corsoy variety 9007 and 9008 Pioneer, Johnston, Iowa), sugar beet (Beta vulgaris L cv NB1xNB4 (United States Agricultural Research Station, Salinas, Calif.) or cv Monohikari (Seedex, Longmont, Colo.), sunflower (*Helianthus anuus*), cabbage (*Brassica oleracea* var. Capitata) and red beet. Radish cv Cherry Bell and Pepper cv Bell Boy were the preferred cultivars for our standard screening assays. Radish was ready for treatment 7 d after planting and yielded significant weight differences 7 d to 14 d after treatment. Radish showed changes in root and shoot yields. Pepper was responsive within a week of treatment. In general, determination of whether a formulation was phytobland or phytotoxic was visibly evident within 5 days. The following plant varieties were treated in commercial greenhouses:

TABLE 1

Exemplary Plants

| | | |
|---|---|---|
| Hypoestes | Dahlia cv Diablo | New Guinea Impatiens |
| Impatiens | Cosmos Sunny Red | Nicotiana cv Domino Purple |
| Pansy | Geranium cv Orbit | White Browalia cv Blue Bell |
| Pepper | Strawberry cv Oso Grande | Eggplant cv Beauty |
| Rue | Portualaca cv Sundial Yellow | Petunia |
| Hibiscus | Coleus cv Wizard Velvet | Parsley |
| Begonia | Torenia cv Clown | Fennel |
| Ageratum | Pepper cv Golden Bell | Oregano |
| Gerbera | Allysum cv Carpet of Snow | Daffodil |
| Snapdragon | Verbena cv Romance Violet | Tulip |
| Gazania | Stock cv Midget Velvet | Pepper cv Sun Bell |
| Fernleaf Dill | Marigold cv Bonanza Orange | Cleome |
| Chamomile | Salvia cv Red Hot Sally | Heucheria |
| Marjorum | Celosia cv Apricot Brandy | Primula cv Pagent Mix |
| Lobelia | Viola cv Sorbet Yellow | Fuchsia |
| Pansy cv Roc Orange | Dianthus cv Princess Mix | *Aster novi-belgii* |
| Kale cv Nagoya Red | Kale cv Nagoya White | Aster cv Professor Kippenberg |
| Kale cv Coral Queen | *Artemisia schmidtiana* | Aster cv Sunrose |
| Hypoestes | Day lily | Bent Grass |
| Salvia cv Sizzler Burgundy | *Polemonium caerulem* Basil | Delphinium cv King Arthur Baron Kentucky Bluegrass |
| Lodgepole Pine | | |

To compare the effects of treatments under tightly controlled conditions, seeds were sown in individual 12 to 16 cm diameter plastic pots containing METRO-MIX® 350 growing medium (Grace Horticultural Products, W.R. Grace & Co., Cambridge, Mass.) or PETER'S® Professional Potting Soil (Scotts-Sierra Horticultural Products Co., Marysville, Ohio) containing complete nutrient pellets (Sierra 17-6-12 Plus Minors, Grace Sierra, Milpitas, Calif.) or fertilizers such as Hoagland nutrients were added regularly as needed. Culture was in controlled environmental growth chambers (16 h light:8 h dark photoperiod, 400–700 $\mu$mol photosynthetically active quantam.m$^{-2}$s$^{-1}$, 24–30° C. and 30% RH) at the University of Massachusetts or the University of Wyoming. Alternatively, plants were cultured in greenhouses with the option of supplemental light provided by 1,000 watt metal halide arc lights (16:8 h photoperiod). In University of Wyoming greenhouses, physical conditions were controlled and in these as well as other greenhouses, treatments and controls being compared were made simultaneously and were subjected to identical conditions consistent with good laboratory practices. Each survey pool held 20 or more replicates per compound tested and these were matched with equal numbers of controls. Plants were generally harvested and analyzed in the vegetative stage within two weeks after treatment. Plants in individual pots received 1 ml to 5 ml of solution per treatment applied with a small hand-held sprayer constructed of an atomizer head attached to a 5 ml syringe or with larger commercial sprayers. Plants in trays received approximately 50 ml of solution per treatment with even distribution and pressures as would be expected of commercial sprayers.

Generally, individual plants received approximately 0.1 ml/cm$^2$ of solution to leaves. Plants were watered daily with measured amounts of purified water.

The performance of compounds was surveyed by comparing yields against untreated controls and 18 mM glycolate+6 mM tyrosine positive controls. Yields were optimized by bracketing around the following concentrations: 10 μM retinoid, 500 μM flavin, 200 μM aminopyrine, 5 mM substituted aryl, 10 mM glycolate and generally 6 mM for others in aqueous solution. Separated active components were included as positive controls to initial tests of mixtures.

Surfactants were compared and phytotoxicity was observed at effective surfactancy levels of TWEEN® 80, HAMPOSYL® C and TRITON® X-100. SILWET® Y14242 surfactant blend effectively wet foliage of plants at 400 ppm to 1200 ppm without phytotoxicity, but concentrations above 2400 ppm reduced growth and caused foliar damage in laboratory and greenhouse investigations. As a standard procedure, 800 ppm Y14242 was added to formulations unless otherwise noted.

Some fertilizers were less effective than others. To test effects of ammonia as compared to nitrate fertilizers, young begonia and radish plants were fed with Hoagland solution nutrients modified to contain either nitrate or ammonia as nitrogen sources. In these preliminary tests comparing nitrogen sources, treatments with pNBA were followed with daily irrigations of 50 ppm nitrate or 50 ppm ammonia modified Hoagland solution nutrients. Growth enhancement was observed with nitrate, but not with ammonia fertilizer; therefore, ammonia fertilizers were eliminated or minimized to 1.5% of the nitrogen nutrient composition or less during the course of the investigations.

For the majority of tests of productivity yield, plants were harvested within 1–4 week(s) of treatment. The plants were removed from pots and the roots were rinsed clean. Shoot and root lengths and fresh and dry weights were determined. Changes in shoot and root growth were recorded in all cases and are variously presented to model growth of plants. Where appropriate, harvested populations were subjected to analysis of variance and mean separation by LSD test and showed significance within 95% confidence limits.

Trials were undertaken in commercial greenhouses to verify practical application methods and beneficial outcome of various treatments. Automated plantings and large populations in commercial settings provided uniformity of results. Plastic trays with up to 512 cells were labeled, filled with media and sown by machine. Transplants to plastic 36 to 48 cell flats were undertaken after 5 to 8 weeks of culture depending on variety and schedules. Media such as BERGER® and METRO® mixes appropriate to the plant types were used to filled cells. Commercial foliar nutrient formulas were applied manually or by automated overhead systems. Irrigation with water was supplied daily, but nutrients were withheld 2 days before and after treatments. Plants in plug trays were generally treated at emergence of the first true leaves. Treatments consisted of foliar sprays and control solutions. Untreated controls were allocated in most cases. Baselines of 100% growth were established for growth of controls as bases for comparisons against each active substance. The percentage of change in growth caused by the tested substance is presented from which the control data can be back-calculated. Mixtures of active materials contained adjuvants because they did not show activity otherwise, therefore, laboratory controls included plants that were treated with the adjuvants at equivalent dilutions. In commercial trials, controls were left untreated. Diseased or aberrant plants were eliminated prior to test. Insects were controlled by regular treatments with appropriate commercial pesticides.

One lead compound, nitrobenzoic acid, is an oxidant and a precursor to pteridines. Initially, we characterized pNBA without pairing it with a reductant. Though effective in laboratory trials, unpaired pNBA was not as consistent in commercial trials as paired pNBA+Reductant formulations. Nitrobenzoates have known relation to CPR and, consistent with our method of selection, pNBA showed high potency and consistent enhancement of plant growth when formulated with reductants. Previous research on nitrobenzoates had been derived from animal liver microsomes (see, for example, H. Sasame, et al., *Mol. Pharmacol.* 5: 123 (1969)); therefore, given our observed plant responses to pNBA, the possibility of plant response to human CPR was examined. Frozen human NADPH:Cytochrome P450 reductase (hCPR) pellets from a recombinant DNA source were diluted in chilled water adjusted to pH 7 to pH 7.5 with dilute KOH. Penetration into cells of foliage by the macromolecular 76.5 kDa enzyme was achieved by addition of sterilized 0.1% CELITE® (diatomaceous earth) kept in suspension with shaking as the mixture was applied to foliage. Hand pumped sprayers were held within 2 to 3 cm of leaf surfaces to maximize pressure and flow of the treatment solution across the leaf surface. Rubbing the solution into the leaves to enhance the microincisive action of CELITE® was required for leaves with thick cuticles such as cabbage, but the spray pressure allowed penetration into pepper and radish leaf cells without additional mechanical intervention. Initially, a concentration gradient was assayed on radish and 10 nM hCPR induced turgidity within an hour, enhancing vegetative yield within two weeks of foliar treatments. Thereafter, 10 nM hCPR was formulated in water adjusted to pH 7.5 with dilute 1 mM KOH, 0.1% CELITE® and 800 ppm Y14242. Formulations were sprayed on foliage within an hour and kept chilled on ice to prevent degradation.

After establishing that foliar treatment with hCPR enhanced plant growth, direct effects of substrates on hCPR and on sugar beet CPR was measured by preparation of microsomes for quantification against CPR and cytochrome c. For the initial preparations, GO+Sali was assayed against hCPR for specific activity. In ensuing preparations, ultracentrifuge-derived microsomal preparations of sugar beet CPR (sbCPR)were assayed against combinations of GO, NAT and FMN as substrates. Preliminary preparation of sugar beets involved germination in growth chambers followed by transplantation to greenhouses. Substrate formulations were dissolved in water with 0.12% Y14242 surfactant blend and sprayed onto the foliage of sugar beets. Controls included equal concentrations of each individual substrate in surfactant and water and untreated plants under otherwise identical conditions of culture. Enzyme assays were undertaken 2 days after treatments. The procedure followed previously described methods (e.g., M. Markwell, et al., *Methods of Enzymology* 72: 296–303 (1981); C. A. Mihaliak, et al., *Methods in plant biochemistry* 19: 261–279 (1993); R. Donaldson, et al., *Arch. Biochem. Biophys.* 152: 199–215 (1972); M. Persans, et al., *Plant Physiol.* 109: 1483–1490 (1995)) and includes a two phase partitioning employing 5.6% polymer concentration with no KCl and the grinding buffer and 0.1 M phosphate assay buffer contained protease inhibitors such as aprotinin (2 mg/mL), amino-n-caproic acid (5 mM), benzamidine HCl (1 mM), leupeptin (2 mg/mL), and pepstatin A (2 mg/mL). Leaves of 54 day-old sugar beet were collected and 24.5 g was weighed and chopped. All preparations were kept chilled at 0–4° C. Chopped leaves were homogenized by mortar and pestle in 100 mL of 50 mM HEPES (pH 7.6), 230 mM sorbitol, 1 mM DTT, 1 mM EDTA, 3 mM EGTA, 0.5% BSA, 10 mM KCl, 5% glycerol, insoluble polyvinylpolypyrrolidone (1.25 mg/mL), 20 mM sodium ascorbate and protease inhibitors. The homogenate was forced through six layers of cheese cloth. The crude microsome pellet was prepared by differential centrifugation. The filtrate was centrifuged three times at 1700×g for 5 min to remove debris. The supernatant was centrifuged at 27K×g for 30 min to sediment mitochondria and chloroplasts. The pellet was resuspended in the assay buffer (3 mL). The supernatant from the 27K×g spin was centrifuged at 75K×g for 1 hr. The crude microsome pellets were saved in 1.2 mL assay buffer. The unused microsomal pellets and 27K×g pellets were resuspended in 0.1 M potassium phosphate (pH 7.4). The pellets, suspensions and the 75K×g supernatant were frozen at −20° C. for later use. Protein contents of microsomes, 75K×g supernatant and 27K×g pellets were determined by a modified Lowry method using BSA as standards. NADPH-dependent reduction of cytochrome c was monitored for increase in absorbancy at 550 nm at room temperature. The incubation medium contained 60 mM phosphate buffer (pH 7.4), NADPH (1 mM), 0.5 mM KCN and microsomes in a 1 mL cuvette with a 1 cm path length. The reaction was initiated by addition of horse heart cytochrome c to a 50 mM final concentration. The absorbancy at 550 nm was measured every 30 seconds for 5 min. One unit is defined as an absorbancy change of 1.0/min at 550 nm at 25° C. in a 1 cm light path. This corresponds to reduction of 0.0476 μmole of cytochrome c per minute per milliliter of reaction mixture. The rate was determined by the difference between the samples with or without NADPH. This method of assay was selected over Cytochrome P450 quantification by CO difference sectroscopy to avoid interference with pigments and sample turbidity. The reaction cocktail contained the following components (0.5 mM KCN was added to inhibit the cytochrome c oxicase activity): water (200 ml), phosphate (600 ml), KCN (50 ml), microsome (50 ml), NADPH (50 ml), cytochrome c (50 ml).

Gas exchange, osmotic potential, enzyme and radioisotope assays were undertaken in the laboratory of Professor John. N. Nishio at the Department of Botany, University of Wyoming, Laramie, Wyo. Photosynthetic $CO_2$ gas exchange was measured with a CIRAS-1 (PP Systems, Bedford, Mass.) portable gas exchange system. Foliage was treated with compounds dissolved in standard aqueous solutions with surfactants. Gas exchange was measured after treatments as a means of checking the health and responsiveness of plants particularly when the tissues were sampled. Gas exchange was nearly doubled in response to some treatments. For quantification of response of plants to stress after treatment with oxidants and reductants, plants were adapted to 23° C., 500 μmole/m²/s light intensity and 80% to 90% humidity for more than 2 weeks prior to the start of the experiment. Photosynthesis and respiration were measured polarographically in a Clark-type Rank oxygen electrode. Foliage was sprayed or compounds were added directly into the oxygen chamber. Formulations and combinations included 100 mM glycolate, 50 mM salicylate, 50 mM pNBA. Specific settings were 1.77 cm² leaf discs, 300 to 400 μm slices, 2 ml of 40 mM HEPES at pH 7, 10 mM sodium bicarbonate in HEPES at pH 7, registration speed 1 cm/min, light intensity 1350 μmol/m²/s, chamber temperature 42° C., adaption of slices to temperature given 5–8 min in room light, and time of zero oxygen was 7 to 12 min. In general, plants treated with oxicant+reductant formulations stood erect with turgidity when placed under environments where controls wilted in midday, indicating that some treatments enhanced tolerance to water stress. Therefore, osmolality was measured with a 5100 B vapor pressure osmometer (Wescor). The osmometer was calibrated with a paper disc and standard plugs were placed in the tray for measurement.

Radioisotopic $^{14}CO_2$ was applied to plants to determine the fate of active substances and changes in the path of carbon fixation. Plant specimens were sprayed with the formulations. At 24 h to 48 h, plants were removed from the glass house and placed under a quartz halogen light (type EKE, 21 V, 150 watt) at room temperature and allowed to acclimate to the laboratory conditions for 15–30 min. To test photorespiration, a leaf was placed in an open chamber that was constantly flushed with pure $O_2$ during the acclimation period. Leaf plugs 3.67 cm² were removed and placed in a hermetically sealed PLEXIGLASS® leaf chamber containing pure $O_2$ being pumped at a rate of 2–3 L/min. To test ambient conditions, air was used instead of pure oxygen gas. The chamber was illuminated with 1,000 μmol photosynthetically active quanta $m^{-2}s^{-1}$ directed through a fiber optic cable connected to a quartz halogen light similar to the one used for preillumination. After 1 min, 5 mL $CO_2$ containing 0.8 μCi $Na^{14}CO_2$ (specific activity of 5 Ci $mol^{-1}$) injected with a syringe to a final concentration of about 700 ppm $CO_2$. The leaf plugs were allowed to incorporate $^{14}CO_2$ for 15, 60 or 180 s, and then fixation was immediately stopped. In other experiments the leaf plugs were pulsed for 15 s, then chased for 1 min or 3 min. The chase was carried out under ambient air. Fixation was stopped by placing the leaf disc in boiling ethanol containing formic acid. Stable fixed $^{14}CO_2$ containing products were separated by paper chromatography as previously described in R. D. Gates, et al., *Proc. Natl. Acad. Sci. USA* 92: 7430–7434 (1995). Protein content of samples was determined by a modified Lowry Procedure, previously described in J. N. Nishio, et al., *Plant Physiol.* 77: 705–711 (1985).

Nuclear magnetic resonance (NMR) $^{13}C$ in vivo studies were undertaken in the laboratory of Professor Roland Douce at the University of Grenoble, Laboratories of Plant Cell Physiology, Centre d'Etudes Nucleaires de Grenoble, CEN-G, 85-X, F-38041 Grenoble Cedex, France utilizing a Bruker AMX400. Uniformly $^{13}C$ labeled glycolate was prepared by Professor A. A. Benson. Solutions of 10 mM $^{13}C$ labeled glycolate+5 mM L-tyrosine+800 ppm Y14242 were prepared and continuously supplied to sycamore cells. Collections of 9 g treated cells were perfused with oxygen and placed in 25 mm diameter tubes. The spectra at 900 scans/hour were taken under the following conditions: 30 μs impulses at 60° and 4 s; decoupler Waltz sequence of 9 watts (0.38 s) with 0.5 watt (3.64 s) period of acquisition. Fourier transform was performed at 16000 points acquired per 16000 zero filling points. Measurements and analyses were compared against reference standards such as hexamethyldisiloxane (resonance peak 2.9 ppm). Other reference resonances corresponded to intracellular compositions typical of 100 μM/g cells.

Results

As shown in Table 2 below, foliar solutions containing nM human CPR (hCPR) or mM CPR substrates enhanced growth significantly. At harvest, plants treated with hCPR and tyrosine were larger and stiffer with turgidity as compared to tyrosine treated and untreated control plants. To the contrary, plants treated with hCPR plus glycolate did not show significantly higher yields than controls, i.e., growth was not enhanced. Glycolate was, therefore, placed in the oxidant category and tyrosine was appropriately placed in the reductant category. Controls were formulated without the active component, but contained equivalent Y14242 and CELITE®. Pepper plants tabulated in Table 2 were grown side-by-side in greenhouses.

TABLE 2

Effects of hCPR and Reductant vs Oxidant

| Compound | ppm | Plant | Fresh Wt. (g/plant) | (%) | Dry Wt. (mg/plant) | (%) |
|---|---|---|---|---|---|---|
| Control | 0 | Pepper | 1.12 | 100 | 121 | 100 |
| hCPR | 0.8 | Pepper | 1.1 | 117 | 129 | 107 |
| Glycolate | 760 | Pepper | 1.22 | 109 | 120 | 100 |
| Tyrosine | 909 | Pepper | 1.19 | 106 | 116 | 96 |
| hCPR + Glycolate | | Pepper | 1.16 | 104 | 120 | 100 |
| hCPR + Tyrosine | | Pepper | 1.41 | 126 | 134 | 111 |

When applied solely, neither oxidants nor reductants showed consistent activity without precise control of environmental conditions. When foliar treatments were balanced with combinations of oxidants plus reductants, the paired formulations enhanced growth significantly and consistently in greenhouses as compared to single component formulations or when compared to untreated controls, shown in Table 3, below. Pansies in Table 3 were treated a month after germination and allowed to grow to bud and bloom. As compared to all of the other experiments in Table 3, the pansy trials represent an unusually long-term study and, therefore, the differences in treated and controlled yields are relatively higher than all other experiments.

TABLE 3

Effect of Separate and Paired Oxidant and Reductant Treatments on Plant Growth

| Compound | ppm | Plant | Fresh Weight (g) | (%) | Dry Weight (mg) | (%) |
|---|---|---|---|---|---|---|
| Control | | All plants | | 100 | | 100 |
| pNBA | 167 | Pansy shoot | 1.2 | 100 | 80 | 101 |
| Aminopyrine | 47 | Pansy shoot | 1.3 | 106 | 100 | 111 |
| pNBA + Aminopyrine | | Pansy shoot | 5.3 | 420 | 300 | 400 |
| pNBA | 200 | Radish shoot | 6.4 | 143 | 300 | 188 |
| Nitromethane | 72 | Radish shoot | 3.8 | 86 | 180 | 110 |
| pNBA + Nitromethane | | Radish shoot | 6.5 | 145 | 420 | 261 |
| pNBA | 50 | Radish shoot | 5.0 | 112 | 220 | 136 |
| Paraffin oil | 510 | Radish shoot | 2.9 | 65 | 60 | 37 |
| pNBA + Paraffin oil | | Radish shoot | 9.3 | 207 | 460 | 287 |
| GO | 2000 | Radish shoot | 5.4 | 126 | 320 | 133 |
| PABA | 70 | Radish shoot | 5.0 | 113 | 300 | 125 |
| GO + PABA | | Radish shoot | 9.6 | 216 | 600 | 258 |
| GO | 1150 | Radish shoot | 5.4 | 126 | 320 | 133 |
| Sali | 690 | Radish shoot | 4.5 | 100 | 240 | 100 |
| GO + Sali | | Radish shoot | 9.3 | 210 | 580 | 242 |
| GO | 115 | Pepper shoot | 1.2 | 109 | 120 | 100 |
| Retinoic | 5 | Pepper shoot | 1.2 | 102 | 120 | 100 |
| GO + Retinoic | | Pepper shoot | 2.0 | 166 | 180 | 150 |
| FMN + FAD | 163 + 207 | Radish shoot | 3.2 | 137 | 160 | 115 |
| Tyrosine | 909 | Radish shoot | 2.5 | 109 | 130 | 102 |
| FMN + FAD + Tyrosine | | Radish shoot | 3.5 | 152 | 150 | 116 |
| GO | 1150 | Pepper shoot | 2.5 | 107 | 250 | 100 |
| Tyrosine | 909 | Pepper shoot | 2.0 | 87 | 240 | 96 |
| GO + Tyrosine | | Pepper shoot | 3.3 | 142 | 360 | 143 |

In all cases examined and shown in Table 3, paired oxidants and reductants showed greater growth enhancement than separate oxidant or reductant treatments. In another related growth experiment, we found that the formulation of FMN+FAD+Tyrosine, given in Table 3, was as effective at increasing pansy shoot dry weight yields (113%) within 10 d as it was at improving radish root yields over controls.

Surveys of different sets of paired oxidants with reductants resulted in enhanced vegetative yields as shown in Table 4, below.

TABLE 4

Effect of Paired Oxidant + Reductant Treatments on Plant Growth

| Compound | ppm | Plant | Fresh Weight (g) | (%) | Dry Weight (mg) | (%) |
|---|---|---|---|---|---|---|
| Control | | All Plants | | 100 | | 100 |
| GO + TyClMe | 3450 + 1390 | Pepper shoot | 4.0 | 151 | 480 | 142 |
| GO + N-Acetyltyrosine | 1150 + 1116 | Radish shoot | 3.4 | 118 | 370 | 118 |
| GO + Tyramine | 1150 + 1000 | Radish shoot | 4.5 | 104 | 290 | 105 |
| GO + AlaTyr | 2000 + 1513 | Pepper shoot | 6.7 | 110 | 920 | 139 |
| GO + Cinnamic | 1150 + 741 | Radish root | 4.3 | 127 | 290 | 115 |
| GO + Ethanol | 115 + 10% | Pepper shoot | 1.3 | 116 | 130 | 108 |
| GO + Orcinol | 2900 + 710 | Pepper shoot | 2.7 | 111 | 290 | 108 |
| GO + Aminopyrine | 1150 + 47 | Impatiens | 47 | 223 | 110 | 211 |
| pNBA + Aminopyrine | 1002 + 47 | Pepper shoot | 2.1 | 117 | 230 | 122 |
| FAM + Aminopyrine | 2000 + 47 | Pepper shoot | 2.8 | 121 | 290 | 117 |
| FAM + TyClMe | 2000 + 1390 | Pepper shoot | 2.3 | 132 | 240 | 130 |
| GO + Manganese | 2000 + 3 | Pepper shoot | 2.6 | 113 | 280 | 115 |
| pNBA + Cinnamic | 1002 + 741 | Pepper shoot | 2.2 | 126 | 230 | 123 |
| FMN + Tyrosine | 120 + 900 | Radish root | 2.2 | 119 | 220 | 146 |
| FMN + Uvinul ® P-25 | 240 + 1265 | Wheat shoot | | 46 | | 119 |

The oxidant+reductant formulation containing glycolic+ salicylic, having been proven effective as a plant growth enhancer (see Table 3), was assayed for effect on the catalyst, CPR. The results of treatment of CPR with glycolic and salicylic acids are given in Table 5 below, in which specific activities, expressed as nanomoles of reduced cytochrome c per minute per mg of protein, are summarized. The pellet referred to in Table 5 is from centrifugation.

TABLE 5 hCPR Specific Activity

| Reductase pellet (treatment) | Specific activity |
|---|---|
| Control 75 K × g pellet | 0.67 |
| GO + Sali 75 K × g pellet | 13.12 |
| 75 K × g supernatant control | 0 |
| 75 K × g supernatant GO + Sali | 0 |
| Control 27 K × g pellet | 0 |
| GO + Sali 27 K × g pellet | 0.08 |

After treatment with GO+Sali, specific activity of the reductase was 20 times higher than the control.

In Table 6, below, the specific activities of oxidants and reductants were measured separately and combined against human CPR and sugar beet CPR. Individual treatments of glycolate and salicylate each increased hCPR activity by 13%, whereas, GO+Sali increased hCPR activity by 20 percent. Similarly, when the specific activities of glycolate, N-acetyltyrosine and FMN were measured separately and combined against microsomal sbCPR, combinations of substrates induced the enzymes more than individual substrates. In fact, when treated with NAT alone, specific activity dropped, but formulations of GO+NAT increased specific acitivity by nearly half-again. Notably, FMN showed significantly higher induction than any other individual substrate tested. The combination of GO+FMN, resulted in higher induction than expected from singular additive effects.

TABLE 6

Reductants and Oxidants Synergistically Enhance Human CPR and Sugar Beet CPR

| Compound | ppm | Plant | CPR Specific Activity | (%) |
|---|---|---|---|---|
| Control, hCPR | | Sugar beet | | 100 |
| Glycolic | 76 | Sugar beet | 1.22 | 113 |
| Salicylic | 90 | Sugar beet | 1.19 | 113 |
| GO + Sali | | Sugar beet | 1.16 | 120 |
| Control, sbCPR | | Sugar beet | | 100 |
| Glycolic | 76 | Sugar beet | 0.026 | 119 |
| N-Acetyltyrosine | 22 | Sugar beet | 0.015 | 67 |
| GO-NAT | | Sugar beet | 0.032 | 146 |
| Control, sbCPR | | Sugar beet | | 100 |
| Glycolic | 76 | Sugar beet | 0.026 | 119 |
| FMN | 25 | Sugar beet | 0.104 | 474 |
| GO + FMN | | Sugar beet | 0.120 | 545 |

In Table 7 below, assimilation rates and assimilation/transpiration (A/T) rates of five soybean plants were measured in the morning 15, 16, and 17 days after treatment. Plants were grown in the greenhouse at the University of Wyoming and measurements were made 57 days from sow date. All 15 measurements per treatment were pooled to calculate average rates (n=15). Probability calculated as a two-tailed Student's T-test is 0.000 for FMN and 0.002 for FAD against controls for A/T supporting the observation that photosynthesis increases for long durations after FMN and FAD treatments.

TABLE 7

FMN and FAD enhance photosynthetic gas exchange for a long duration.

| Treatment | Time After Spray | Assimilation ($\mu mol \cdot m^{-2} \cdot s^{-1}$) | Assimilation (T/C) | A/T | A/T (T/C) |
|---|---|---|---|---|---|
| Control (n = 5) | 15 d | 7.2 ± 1.1 | — | 1.71 ± 0.25 | — |
| | 16 d | 8.7 ± 1.9 | — | 1.58 ± 0.24 | — |
| | 17 d | 8.7 ± 1.9 | — | 1.8 ± 0.26 | — |
| Pooled average | | 8.2 ± 2.1 | | 1.69 ± 0.27 | |
| FMN (125 ppm) | 15 d | 10.5 ± 2.9 | 1.46 ± 0.40 | 2.49 ± 0.28 | 1.46 ± 0.16 |
| (n = 5) | 16 d | 9.9 ± 1.8 | 1.14 ± 0.21 | 2.07 ± 0.21 | 1.31 ± 0.13 |
| | 17 d | 9.8 ± 2.4 | 1.13 ± 0.27 | 2.12 ± 0.16 | 1.14 ± 0.20 |
| Pooled average | | 10.1 ± 2.4 | | 2.20 ± 0.35 | |
| FAD (200 ppm) | 15 d | 8.4 ± 3.4 | 1.16 ± 0.47 | 2.18 ± 0.46 | 1.27 ± 0.27 |
| (n = 5) | 16 d | 10.4 ± 2.6 | 1.20 ± 0.30 | 1.99 ± 0.36 | 1.26 ± 0.23 |
| | 17 d | 10.7 ± 2.1 | 1.23 ± 0.25 | 2.12 ± 0.16 | 1.18 ± 0.09 |
| Pooled average | | 9.8 ± 3.0 | | 2.09 ± 0.36 | |

Plants treated with 125 ppm FMN showed a higher degree of turgidity than controls, especially when controls showed signs of water stress. Water potential of FMN-treated sugar beets and controls was measured with an osmometer. FMN-treated sugar beet showed improved water potential values, an average of 3 plant measurements at −3.83 milliPascals, as compared to controls which averaged −4.71 milliPascals. Probability calculated as a two-tailed Student's T-test was 0.058.

In Table 8, below, pepper plants were treated with 10 mM GO+2.5 mM Tyr+800 ppm Y14242. Gas exchange was measured under clear morning skies in a glass greenhouse. Table 8 shows two runs of the experiment that were undertaken. Carbon dioxide uptake occurred at significantly higher rates in plants treated with GO+Tyr as compared with untreated controls.

TABLE 8

Glycolate + Tyrosine increase carbon dioxide uptake

| Treatment | $CO_2$ Dif | Assimilation |
|---|---|---|
| Control 1 average | −15.82 | 7.68 |
| STD | 4.51 | 2.19 |
| GO + Tyr 1 average | −25.60 | 12.33 |
| STD | 3.36 | 1.94 |
| Control 2 average | −18.82 | 9.06 |
| STD | 6.05 | 2.98 |
| GO + Tyr 2 average | −26.73 | 13.27 |
| STD | 3.20 | 1.65 |

Further characterization of glycolate+L-tyrosine treatments showed quantifiably higher osmotic pressure corresponding to visually observed turgidity enhancement over controls. Pepper plants that were treated with GO+Tyr showed an improved osmotic pressure of −24.3 Bars as compared to controls without treatments that showed an osmotic pressure of −21.1 Bars. The improved osmotic pressures measured for GO+Tyr treatment corresponded to the visual observations of clearly higher turgidity in treated plants in contrast to wilted untreated controls.

Plants that were treated with pairs of oxidant+reductant tolerated stress with enhanced photosynthesis as compared with controls and as shown in Table 9, below. Consistent with other plant responses, the data in Table 9 shows that treatments with substrates of CYP and CPR enhance photosynthetic oxygen evolution ($\mu mol/m^2/s$). When oxidase and reductase substrates are combined at appropriate ratios and concentrations, enhancement is greater than when either substrate is added alone.

TABLE 9

Effect of Cytochrome P450 Substrates on Oxygen Evolution and Stress

| | | Before $O_2$ and Light Stress | | | After $O_2$ and Light Stress | | | |
|---|---|---|---|---|---|---|---|---|
| Species | Compound | Dark | Light | Gross | Dark | Light | Gross | Ratio |
| Red beet | Control | −6.66 + 1.04 | 10.44 + 0.99 | 17.1 + 2.03 | −5.4 + 0.42 | −0.27 + 0.03 | 5.13 + 0.39 | 30.08 |
| Red beet | GO + Sali | −7.4 ± 0.52 | 10.95 ± 1.7 | 18.35 ± 2.22 | −6.18 ± 0.36 | 0.93 ± 0.05 | 7.11 ± 0.41 | 38.75 |
| Red beet | Control | −3.48 ± 0.13 | 10.01 ± 1.02 | 13.49 ± 1.15 | −3.24 ± 0.22 | 0.3 ± 0.01 | 3.54 ± 0.05 | 26.24 |
| Red beet | GO 100 μM | −4.09 ± 0.17 | 10.88 ± 1.61 | 14.97 ± 1.78 | −3.08 ± 0.21 | 1.3 ± 0.1 | 4.38 ± 0.31 | 29.26 |
| Red beet | Sali 50 μM | −3.89 ± 0.45 | 10.07 ± 0.47 | 13.96 ± 0.92 | −3.12 ± 0.05 | 1.26 ± 0.02 | 4.38 ± 0.07 | 31.38 |
| Red beet | GO + Sali | −4.09 ± 0.17 | 11.71 ± 1.85 | 15.8 ± 2.08 | −3.52 ± 0.18 | 1.48 ± 0.06 | 5 ± 0.24 | 31.65 |
| Red beet | Control 2 | 3.81 ± 0.07 | 12.08 ± 1.32 | 15.89 ± 1.39 | −3.08 ± 0.21 | 1 ± 0.05 | 4.08 ± 0.26 | 25.68 |
| Red beet | Control | −2.25 ± 0.16 | 6.91 ± 0.3 | 9.16 ± 0.46 | −1.73 ± 0.1 | −0.08 ± 0.01 | 1.65 ± 0.09 | 18.01 |
| Red beet | 0.1 mM GO + Tyr | −2.68 ± 0.1 | 7.87 ± 0.38 | 10.55 ± 0.48 | −2.42 ± 0.08 | 1.6 ± 0.09 | 4.02 ± 0.17 | 38.1 |
| Red beet | 1 mM GO + Tyr | −2.31 ± 0.24 | 7.63 ± 0.72 | 9.94 ± 0.96 | −2.01 ± 0.06 | 1.22 ± 0.02 | 3.23 ± 0.08 | 32.49 |
| Cabbage | Control | −2.57 ± 0.16 | 10.44 ± 0.99 | 13.01 ± 1.15 | −2.87 ± 0.09 | −0.79 ± 0.05 | 2.08 ± 0.04 | 15.99 |
| Cabbage | GO + Sali | −2.63 ± 0.08 | 4.02 ± 0.64 | 6.65 ± 0.72 | −2.74 ± 0.08 | 0.2 ± 0.05 | 2.94 ± 0.13 | 44.21 |
| Cabbage | Control | −2.9 ± 0.04 | 10.39 ± 0.01 | 13.29 ± 0.05 | −3.01 ± 0.11 | −0.46 ± 0.05 | 2.55 ± 0.06 | 19.19 |
| Cabbage | GO + Sali | −2.87 ± 0.09 | 10.69 ± 0.4 | 13.56 ± 0.49 | −2.97 ± 0.05 | 0.24 ± 0.02 | 3.21 ± 0.07 | 23.67 |
| Soy bean | Control | −2.7 ± 0.33 | 13.61 ± 0.85 | 16.31 ± 1.18 | −3.01 ± 0.11 | 1.77 ± 0.06 | 4.78 ± 0.17 | 29.31 |
| Soy bean | GO + Sali | −3.08 ± 0.21 | 14.33 ± 1.86 | 17.41 ± 2.07 | −3.52 ± 0.07 | 5.61 ± 0.45 | 9.13 ± 0.52 | 52.44 |
| Soy bean | Control | −2.54 ± 0.37 | 9.53 ± 2.28 | 12.07 ± 2.65 | −2.43 ± 0.05 | 2.22 ± 0.16 | 4.65 ± 0.21 | 38.53 |
| Soy bean | GO + Sali | −3.16 ± 0.32 | 10.44 ± 0.99 | 13.6 ± 1.31 | −2.87 ± 0.09 | 6.37 ± 0.94 | 9.24 ± 1.03 | 67.94 |

NMR spectra of glycolate and tyrosine treated sycamore cells elucidated inhibitory action of the paired formulation. Without tyrosine, the $^{13}C$ labeled glycolate was passed on to other metabolites. Preabsorbed tyrosine inhibited metabolism of $^{13}C$ labeled glycolate in nonphotosynthetic sycamore cells.

Discussion

Our results show that when CYP and CPR are induced, photosynthesis and plant growth are enhanced. With few exceptions, when either of the CYP or CPR substrates was supplied without the necessary electron couple or enzyme partner, treatments were ineffective or inconsistent. The most potent treatment was foliar nanomolar CPR with reductant substrates such as tyrosine. Of the CPR substrates which stimulated growth at μM concentrations, FMN may be ranked as the most practical oxidant, being both safe and effective. In all cases, CYP inducers did not enhance growth as much as when applied with CPR or its substrates; however, induction of human CPR with oxidants and reductants indicates a deeper tandem involvement of the reductase than had been known previously. Results that showed paired treatments enhanced gas exchange are consistent with inhibition of glycolate metabolism observed by NMR. Furthermore, physiological and biochemical enhancement caused by treatments are descriptive of plant growth and yield enhancements in the long term. Our studies provide conclusive evidence that induction of cytochromes P450 is key to plant growth.

Formulations that coupled pNBA with reductants generally showed high potency and consistently higher yields than other pairs. The observed plant responses to human CPR by coapplication of the enzyme with reductants in our experiments was consistent with our hypothesis for the role of pNBA. Selection of reductants and oxidants based on one electron reduction of compounds (see, e.g., P. Wardman, *J. Phys. Chem. Ref. Data* 18(4): 1637–1755 (1989)) within potentials associated with CPR reductase (see, e.g., J. Butler, et al., *Biochimica et Biophysica Acta* 1161: 73 (1993)) proved successful given the substrates we discovered to improve yields. The combinations of cytochromes P450 reductases with monooxygenase substrates are numerous and underscore the potential of the field.

Photorespiration is a universal plant response to light, heat, $O_2$ and $CO_2$. N. Tolbert, et al., *Proc. Natl. Acad. Sci. USA* 92: 11230–11233 (1995). Radicals generated during photorespiration damage the photosynthetic apparatus. By nature of its interference, once photorespiration is controlled, enhanced productivity of all plants becomes possible. In our studies, growth of plants was enhanced under conditions favoring photorespiration after foliar treatments with formulations designed to enhance CPR and CYP. Photorespiration is a major endogenous source of glycolate and this chemical imbalance sends signals to stop related metabolic functions. A. Angerhofer, et al., *Photochemistry and Photobiology* 63: 11–38 (1996). From our nuclear magnetic resonance studies, inhibition of exogenous glycolate metabolism was evident. Glycolate production inhibits $CO_2$ fixation. See, M. Badger, et al., *Photosynthesis Research* 37: 177–191 (1993); A. Miller, et al., *Plant Physiol.* 91: 1044–1049 (1989); T. Takabe, et al., *Biochemistry* 19: 3985–3989 (1980); and C. Wendler, et al., *J. Plant Physiol.* 139: 666–671 (1992). In contrast, when we combined foliar applications of glycolate with CYP reductants, we observed increased $CO_2$ fixation and enhanced tolerance to the photorespiratory stimuli. Initially, we selected glycolate as an electron donor, but to our surprise, we observed that 5 mM to 30 mM glycolate concentrations synergistically enhanced the activity of reductants, but not oxidants.

Work over the past decades has taken our knowledge of cytochromes P450 from identifying enzymes without function to highly characterized proteins with defined catalytic electron transfer functions. See, C. von Wachenfeldt, et al., *Structures of Eukaryotic Cytochrome P450 Enzymes*, P. R. Ortiz de Montellano, ed. (1995) CYTOCHROME P450: STRUCTURE, MECHANISM, AND BIOCHEMISTRY (Second Ed.), Plenum Press, New York, pp 183–223 and H. Strobel, et al., *NADPH Cytochrome P450 Reductase and Its Structural and Functional Domains*, P. R. Ortiz de Montellano, ed. (1995) CYTOCHROME P450: STRUCTURE, MECHANISM, AND BIOCHEMISTRY (Second Ed.) Plenum Press, New York, pp 225–244. Exploitation of CYP has not previously been reduced to practice in plants, but from investigations of biochemical pathways, it has been known that CYP enzymes are involved in the metabolism of single carbon fragments, abscisic acid, ethylene, gallic acid, cytokinin, lignin, furanocoumarin, anthocyanin, gibberellic acid, limonene, geraniol, nerol, dhurrin, bisbenzylisoquinoline alkaloids, jasmonic acid, phophonomethylglycine, sulfonylurea, phenylurea, aryloxyphenoxypropionate, metflurazon, sethoxydim, bentazon and insecticides. See, M. Schuler, *Critical Reviews in Plant Sciences* 15(3): 235–284 (1996). Some compounds which may be metabolized into phytotoxic compounds, might enhance herbicidal action. For example, if activity of a reductant herbicide is targeted, then formulating it with an oxidant such as N-3-nitrophenyl-N'-phenylurea may speed its action. Furthermore, oxidants such as pNBA, 1,4-bis[(2-ethylhexyl)amino]anthraquinone or 1,4-bis(2-methylanilino)anthraquinone may be compatible with a reductant herbicide such as phosphonomethylglycine. Our methods are also appropriate to stimulate enhancement of blooms. Interaction of N-phenylcarbamates with CYP has been shown to induce flowering in asparagus seedlings. See, M. Kusukawa, et al., *Z. Naturforsch* 50c: 373–379 (1995). The results of our experiments with formamidines support the relationship of CYP to flowering, combinations of oxidants with reductant formamidines showing potential for floricultural product development.

Of the reductants that we surveyed for pairing, tyrosine is notable. Without oxidant additions, the effects of tyrosine on plant growth were inconsistent. In our experiments the derivative of tyrosine with the highest electron reduction potential, tyrosine methyl ester (870 mV) showed the most consistent plant responses as compared against those with lower electron potentials. Combinations of tyrosines with pNBA, glycolate, FMN, and FAD yielded nontoxic and practical formulations.

The requirement that we have shown for electron couples to elicit plant growth responses is consistent with monoxygenase and reductase necessary for metabolism of typical human cytochromes P450 substrates in bacteria. Transformed *Escherichia coli* metabolized monooxygenase substrates when CPR reductase was coexpressed with CYP monoxygenase (A. Parikh, et al., *Nature Biotechnology* 15: 784–788 (1997)), in this case, accomplished with a bicistronic vector. Expression of intergeneric cloning of yeast CPR reductase has been demonstrated. See, E. Kargel, et al., *Yeast* 12: 333–348 (1996). Specific CPR reductase sequences encoded for glycolate, once isolated, may find expression during periods of light saturation. For example, tyrosines are closely associated with CYP (see, e.g., B. Halkier, et al., *Plant Physiol.* 96: 10–17 (1991)), and in fact, all forms of tyrosine that we tested showed consistent growth responses when paired with reductants. The reaction center of the photosystem II oxygenic electron transport chain contains two redox-active tyrosines, Tyr160 Y sub D and Tyr161 Y sub Z (see, e.g, G. MacDonald, et al., *Proc. Natl. Acad. Sci. USA* 90: 11024–11028 (1993)) and these tyrosines are involved as electron donors to the water-oxidizing complex of photosynthesis in the cytochrome c mediated reduction of photooxidized chlorophyll. See, J. Wachtveitl, et al., *Biochemistry* 32: 10894–10904 (1993). Given the fundamental relationship of tyrosine to photosynthesis in association with the primary sequence of CYP P450tyr (see, B. Koch, et al., *Archives of Biochemistry and Biophysics* 323: 177–186 (1995)), plants might be genetically altered and bred for increased levels of the enzymes associated with such CYP functions. For example, if expression of CYP P450tyr is engineered to be triggered by photorespiration, the inhibition of glycolate we observed by exogenous application of tyrosine may prove as beneficial to the enhancement of plant growth as that which we observed in growth studies. Expression of an oxygen transport complex foreign to plants, such as hemoglobin, has been demonstrated in tobacco by fusion of coding sequences of globins to chloroplastidic transit peptide of the small subunit of Rubisco from pea. See, W. Dieryck, et al., *Nature* 386: 29–30 (1997). Transgenic tobacco expressing haemoglobin exhibits enhanced growth and metabolites. See, N. Holmberg, *Nature Biotechnology* 15: 244–247 (1997). Similar techniques may be applied for the insertion and amplified expression of coding sequences for CYP to give long-term results similar to our foliar treatments.

Based on the results of our biochemical, physiological and growth studies, we conclude that our treatments of plants to induce CYP and CPR cause increases in the rate and quantity of carbon fixation. The ubiquity of CYP and CPR provides universal applicability of these compositions and methods for selection of components which endows plants with a means of resistance to environmental and chemical stresses while gaining ever greater photosynthetic productivity for all plants.

The foregoing is illustrative of the present invention and is not to be construed as limiting thereof. The invention is defined by the following claims, with equivalents of the claims to be included therein.

That which is claimed is:

1. A method for enhancing growth of a plant, said method comprising:
    (a) applying to said plant a first compound selected from the group consisting of (i) NADPH:cytochrome P450 reductase and (ii) oxidants that induce NADPH:cytochrome P450 reductase in plants; and
    (b) applying to said plant a second compound selected from the group consisting of (i) cytochrome P450 monooxygenase and (ii) reductants that induce cytochrome P450 monooxygenase.

2. The method according to claim 1, wherein said first compound is an oxidant that induces NADPH:cytochrome P450 reductase selected from the group consisting of glycolate, flavin mononucleotide, riboflavin, p-nitrobenzoic acid, p-nitrophenolate, and combinations thereof.

3. The method according to claim 1, wherein said second compound is a reductant that induces cytochrome P450 monooxygenase selected from the group consisting of cytochromes, amines, cinnamates, retinoids, fatty acids, pteridines, terpenoids, alcohols, ketones, pyridines, indoles, brassinolides, barbiturates, and combinations thereof.

4. The method according to claim 3, wherein said reductant is selected from the group consisting of hemoglobin, tyrosine, tyrosine ester, tyrosine methylester, tyrosine methylester hydrochloride, tyramine, alanyltyrosine, aminopyrine, phosphonomethyl glycine, salicylates, trans-retinoic acid, carbamate, p-aminobenzoic acid, PEG-25 p-aminobenzoic acid, indole-3-glycerol phosphate, methanol, acetone, phenobarbital, and combinations thereof.

5. The method according to claim 1, wherein said second compound is selected from the group consisting of tyrosine methylester, tyrosine methylester hydrochloride, aminopyrine, p-aminobenzoic acid, and PEG-25 p-aminobenzoic acid.

6. The method according to claim 1, wherein the first compound is p-nitrobenzoic acid and the second compound is tyrosine methylester hydrochloride.

7. The method according to claim 1, wherein the first compound is p-nitrobenzoic acid and the second compound is PEG-25 p-aminobenzoic acid.

8. The method according to claim 1, wherein the first compound is glycolate and the second compound is tyrosine methylester hydrochloride.

9. A method for enhancing growth of a plant, said method comprising applying to said plant NADPH:cytochrome P450 reductase and cytochrome P450 monooxygenase, wherein said method enhances growth of said plant.

10. A method for enhancing growth of a plant, said method comprising:
    (a) applying to said plant an oxidant that induces NADPH:cytochrome P450 reductase in plants, wherein said oxidant is selected from the group consisting of flavins; salts of flavins; hydrates of flavins; surfactant-linked derivatives of flavins; and combinations thereof; and (b) applying to said plant a reductant that induces cytochrome P450 monooxygenase.

11. The method according to claim 10, wherein said oxidant has an $E_0$ value of between about −400 mV and about −165 mV.

12. The method according to claim 10, wherein said reductant has an $E_0$ value of between about 1 and about 2000 mV.

13. The method according to claim 10, wherein said oxidant is selected from the group consisting of flavin mononucleotide, flavin adenine dinucleotide, riboflavin, deazaflavin, salts thereof, hydrates thereof, surfactant-linked derivatives thereof, and combinations thereof.

14. The method according to claim 10, wherein said oxidant is flavin mononucleotide.

15. The method according to claim 10, wherein said reductant is selected from the group consisting of cytochromes, amines, cinnamates, retinoids, fatty acids, pteridines, terpenoids, alcohols, ketones, pyridines, indoles, brassinolides, barbiturates, and combinations thereof.

16. The method according to claim 10, wherein said reductant is selected from the group consisting of hemoglobin, tyrosine, tyrosine ester, tyrosine methylester, tyrosine methylester hydrochloride, tyramine, alanyltyrosine, aminopyrine, phosphonomethyl glycine, salicylates, trans-retinoic acid, carbamate, p-aminobenzoic acid, PEG-25 p-aminobenzoic acid, indole-3-glycerol phosphate, methanol, acetone, phenobarbital, and combinations thereof.

17. The method according to claim 10, wherein said reductant is selected from the group consisting of p-aminobenzoic acid, PEG-25 p-aminobenzoic acid, aminopyrine, tyrosine methylester, and tyrosine methylester hydrochloride.

18. The method according to claim 10, wherein said oxidant is flavin mononucleotide and said reductant is tyrosine methylester hydrochloride.

19. The method according to claim 10, wherein said oxidant is flavin mononucleotide and said reductant is p-aminobenzoic acid.

20. The method according to claim 10, wherein said oxidant is flavin mononucleotide and said reductant is PEG-25 p-aminobenzoic acid.

21. The method according to claim 10, wherein said oxidant and said reductant are applied in an amount effective to increase the amount of cytochrome P450 in tyrosine methylester hydrochloride, tyramine, alanyltyrosine, aminopyrine, phosphonomethyl glycine, salicylates, trans-retinoic acid, carbamate, p-aminobenzoic acid, PEG-25 p-aminobenzoic acid, indole-3-glycerol phosphate, methanol, acetone, phenobarbital, and combinations thereof.

22. The method according to claim 10, wherein said oxidant and said reductant are applied to said plant at a location selected from the group consisting of leaves, shoots, roots, seed and stem.

23. The method according to claim 10, wherein said oxidant and said reductant are applied to one or more leaves of said plant.

24. The method according to claim 10, wherein said oxidant and said reductant are applied to plant tissue selected from the group consisting of cell suspensions, callus tissue cultures, and micropropagation cultures.

25. The method according to claim 10, wherein said method further comprises the step (c) of applying a fertilizer to said plant.

26. The method according to claim 25, wherein said fertilizer is selected from the group consisting of (i) $C_1$–$C_7$ alkyl glucosides, and (ii) nitrogenous fertilizers containing not more than 1.5% ammoniacal nitrogen.

27. A method for enhancing growth of a plant, said method comprising applying to the foliage of said plant, a composition comprising (i) a growth enhancing effective amount of a plant growth regulator selected from the group consisting of tyrosine, tyrosine ester, cytochrome P450 tyrosine, tyrosine methylester, and tyrosine methylester hydrochloride and (ii) an agronomically suitable surfactant.

28. A method for enhancing growth of a plant, said method comprising applying to the foliage of said plant, a composition comprising (i) a growth enhancing effective amount of a flavin selected from the group consisting of flavin mononucleotide, flavin adenine dinucleotide, riboflavin, deazaflavin, salts thereof, hydrates thereof, surfactant-linked derivatives thereof, and combinations thereof, and (ii) an agronomically suitable surfactant.

29. The method according to claim 28, wherein said composition further comprises glycolate.

30. A plant growth enhancing system comprising:
  (a) an aqueous solution containing an amount of an oxidant which induces NADPH:cytochrome P450 reductase in said plant, wherein said oxidant is selected from the group consisting of flavins; salts of flavins; hydrates of flavins; surfactant-linked derivatives of flavins; and combinations thereof; and
  (b) an aqueous solution containing an amount of a reductant which induces cytochrome P450 monooxygenase in said plant.

31. The system according to claim 30, wherein said oxidant is selected from the group consisting of flavin mononucleotide, flavin adenine dinucleotide, riboflavin, deazaflavin, salts thereof, hydrates thereof, surfactant-linked derivatives thereof, and combinations thereof.

32. The system according to claim 30, wherein said reductant is selected from the group consisting of cytochromes, amines, cinnamates, retinoids, fatty acids, pteridines, terpenoids, alcohols, ketones, pyridines, indoles, brassinolides, barbiturates, and combinations thereof.

33. The system according to claim 30, wherein said reductant is selected from the group consisting of hemoglobin, tyrosine, tyrosine ester, tyrosine methylester, tyrosine methylester hydrochloride, tyramine, alanyltyrosine, aminopyrine, phosphonomethyl glycine, salicylates, trans-retinoic acid, carbamate, p-aminobenzoic acid, PEG-25 p-aminobenzoic acid, indole-3-glycerol phosphate, methanol, acetone, phenobarbital, and combinations thereof.

34. The system according to claim 30, wherein said oxidant is flavin mononucleotide and said reductant is tyrosine methylester hydrochloride.

35. The system according to claim 30, wherein said oxidant is flavin mononucleotide and said reductant is p-aminobenzoic acid.

36. The system according to claim 30, wherein said oxidant is flavin mononucleotide and said reductant is PEG-25 p-aminobenzoic acid.

37. A composition for enhancing growth of a plant, said composition comprising:
  (a) a first compound selected from the group consisting of (i) NADPH:cytochrome P450 reductase and (ii) oxidants that induce NADPH:cytochrome P450 reductase in plants; and
  (b) a second compound selected from the group consisting of tyrosine, tyrosine ester, and salts thereof.

38. The composition according to claim 37, wherein said second compound is selected from the group consisting of tyrosine methylester and tyrosine methylester hydrochloride.

* * * * *